(12) United States Patent
Pandolfi et al.

(10) Patent No.: US 10,443,055 B2
(45) Date of Patent: Oct. 15, 2019

(54) COMPOUNDS THAT TARGET MYC MICRORNA RESPONSIVE ELEMENTS FOR THE TREATMENT OF MYC-ASSOCIATED CANCER

(71) Applicant: BETH ISRAEL DEACONESS MEDICAL CENTER, Boston, MA (US)

(72) Inventors: Pier Paolo Pandolfi, Boston, MA (US); Assaf C. Bester, Boston, MA (US); Yvonne Tay, Singapore (SG)

(73) Assignee: BETH ISRAEL DEACONESS MEDICAL CENTER, Boston, MA (US)

( * ) Notice: Subject to any disclaimer, the term of this patent is extended or adjusted under 35 U.S.C. 154(b) by 0 days.

(21) Appl. No.: 15/845,573

(22) Filed: Dec. 18, 2017

(65) Prior Publication Data

US 2018/0195067 A1 Jul. 12, 2018

Related U.S. Application Data

(60) Provisional application No. 62/438,303, filed on Dec. 22, 2016.

(51) Int. Cl.
| | | |
|---|---|---|
| *C07H 21/04* | (2006.01) | |
| *C12N 15/113* | (2010.01) | |
| *A61P 35/00* | (2006.01) | |

(52) U.S. Cl.
CPC ............ *C12N 15/113* (2013.01); *A61P 35/00* (2018.01); *C12N 15/1135* (2013.01); *C12N 2310/141* (2013.01); *C12N 2310/315* (2013.01); *C12N 2310/321* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,328,470 A | 7/1994 | Nabel et al. | |
| 5,684,143 A | 11/1997 | Gryaznov et al. | |
| 5,858,988 A | 1/1999 | Wang | |
| 6,107,094 A | 8/2000 | Crooke | |
| 6,168,587 B1 | 1/2001 | Bellhouse et al. | |
| 6,177,403 B1 | 1/2001 | Stedman | |
| 6,194,389 B1 | 2/2001 | Johnston et al. | |
| 6,291,438 B1 | 9/2001 | Wang | |
| 6,471,996 B1 | 10/2002 | Sokoll et al. | |
| 6,472,375 B1 | 10/2002 | Noon et al. | |
| 7,459,547 B2 | 12/2008 | Zamore et al. | |
| 7,732,593 B2 | 6/2010 | Zamore et al. | |
| 7,750,144 B2 | 7/2010 | Zamore et al. | |
| 7,772,203 B2 | 8/2010 | Zamore et al. | |
| 8,304,530 B2 | 11/2012 | Zamore et al. | |
| 8,309,704 B2 | 11/2012 | Zamore et al. | |
| 8,309,705 B2 | 11/2012 | Zamore et al. | |
| 8,329,892 B2 | 12/2012 | Zamore et al. | |
| 9,506,060 B2* | 11/2016 | Bandaru | C12N 15/1135 |
| 2005/0220766 A1 | 10/2005 | Amalfitano et al. | |
| 2006/0078542 A1 | 4/2006 | Mah et al. | |
| 2007/0259827 A1 | 11/2007 | Aronin et al. | |
| 2008/0269149 A1 | 10/2008 | Bowles et al. | |
| 2010/0186103 A1 | 7/2010 | Gao et al. | |
| 2014/0296486 A1 | 10/2014 | Gao et al. | |
| 2016/0281091 A1* | 9/2016 | Brown | C12N 15/1135 |
| 2017/0283807 A1* | 10/2017 | Mounir | C12N 15/1137 |

OTHER PUBLICATIONS

Alisky et al. (2000) "Gene Therapy for Amyotrophic Lateral Sclerosis and Other Motor Neuron Diseases," Human Gene Ther. 11:2315-2329.
Ambros et al. (2003) "MicroRNAs and other tiny endogenous RNAs in C. elegans," Curr. Biol. 13(10):807-18.
Bagella et al. (1998) "Cloning of murine CDK9/PITALRE and its tissue-specific expression in development," J. Cell. Physiol. 177(2):206-13.
Beroukhim et al. (2010) "The landscape of somatic copy-number alteration across human cancers," Nature. 463:899-905.
Billy et al. (2001) "Specific interference with gene expression induced by long, double-stranded RNA in mouse embryonal teratocarcinoma cell lines," Proc. Natl. Acad. Sci. USA. 98(25):14428-33.
Braasch et al. (2003) "RNA interference in mammalian cells by chemically-modified RNA," Biochemistry. 42:7967-7975.
Brennecke et al. (2003) "bantam encodes a developmentally regulated microRNA that controls cell proliferation and regulates the proapoptotic gene hid in *Drosophila*," Cell. 113(1):25-36.
Brennecke et al. (2003) "Towards a complete description of the microRNA complement of animal genomes," Genome Biol. 4(9):228. pp. 1-3.
Brummelkamp et al. (2002) "A system for stable expression of short interfering RNAs in mammalian cells," Science. 296:550-553.
Calegari et al. (2002) "Tissue-specific RNA interference in postimplantation mouse embryos with endoribonuclease-prepared short interfering RNA," Proc. Natl. Acad. Sci. USA. 99(22):14236-40.
Chen et al. (1994) "Gene therapy for brain tumors: regression of experimental gliomas by adenovirus-mediated gene transfer in vivo," Proc. Natl. Acad. Sci. USA. 91:3054-3057.
Davidson et al. (1993) "A model system for in vivo gene transfer into the central nervous system using an adenoviral vector," Nat. Genet. 3:219-223.
Davidson et al. (2000) "Recombinant adeno-associated virus type 2, 4, and 5 vectors: transduction of variant cell types and regions in the mammalian central nervous system," Proc. Natl. Acad. Sci. USA. 97:3428-3432.

(Continued)

*Primary Examiner* — Kimberly Chong
(74) *Attorney, Agent, or Firm* — Lathrop Gage LLP; James H. Velema, Esq.

(57) ABSTRACT

Novel mIR-330 agents and their methods of use are provided. Methods of treating MYC-associated cancers are provided.

13 Claims, 30 Drawing Sheets
Specification includes a Sequence Listing.

(56) References Cited

OTHER PUBLICATIONS

Eckstein (2000) "Phosphorothioate oligodeoxynucleotides: what is their origin and what is unique about them?" Antisense Nucleic Acid Drug Dev. 10(2):117-21.
Elmen et al. (2005) "Locked nucleic acid (LNA) mediated improvements in siRNA stability and functionality," Nucleic Acids Res. 33(1):439-447.
Fattal et al. (1998) "Biodegradable polyalkylcyanoacrylate nanoparticles for the delivery of oligonucleotides," J. Control Release 53(1-3):137-43.
Fisher et al. (1996) "Transduction with recombinant adeno-associated virus for gene therapy is limited by leading-strand synthesis," J Virol. 70:520-532.
Gabay et al. (Jun. 2, 2014) "MYC activation is a hallmark of cancer initiation and maintenance," Cold Spring Harb. Perspect. Med. 4:a014241.
Godard et al. (1995) "Antisense effects of cholesterol-oligodeoxynucleotide conjugates associated with poly(alkylcyanoacrylate) nanoparticles," Eur. J. Biochem. 232(2):404-10.
Grad et al. (2003) "Computational and experimental identification of C. elegans microRNAs," Mol. Cell. 11(5):1253-63.
Griffiths-Jones (2004) "The microRNA Registry," Nuc. Acids Res. 32(Database issue):D109-11.
Hamajima et al. (1998) "Intranasal administration of HIV-DNA vaccine formulated with a polymer, carboxymethylcellulose, augments mucosal antibody production and cell-mediated immune response," Clin. Immunol. Immunopathol. 88(2):205-10.
Herdewijn (2000) "Heterocyclic modifications of oligonucleotides and antisense technology," Antisense Nucleic Acid Drug Dev. 10(4):297-310.
Jacque et al. (2002) "Modulation of HIV-1 replication by RNA interference," Nature. 418(6896):435-8.
Lagos-Quintana et al. (2001) "Identification of novel genes coding for small expressed RNAs," Science. 294(5543):853-8.
Lagos-Quintana et al. (2002) "Identification of tissue-specific microRNAs from mouse," Curr. Biol. 12(9):735-9.
Lagos-Quintana et al. (2003) "New microRNAs from mouse and human," RNA. 9(2):175-9.
Lai et al. (2003) "Computational identification of *Drosophila* microRNA genes," Genome Biol. 4(7):R42. pp. 1-20.
Lam et al. (1991) "A new type of synthetic peptide library for identifying ligand-binding activity," Nature. 354:82-84.
Lambert et al. (2001) "Nanoparticulate systems for the delivery of antisense oligonucleotides," Drug Deliv. Rev. 47(1):99-112.
Langa et al. (2001) "Healthy mice with an altered c-myc gene: role of the 3' untranslated region revisited," Oncogene. 20:4344-4353.
Lau et al. (2001) "An abundant class of tiny RNAs with probable regulatory roles in Caenorhabditis elegans," Science. 294(5543):858-62.
Lee et al. (2001) "An extensive class of small RNAs in Caenorhabditis elegans," Science. 294(5543):862-4.
Lee et al. (2002) "Expression of small interfering RNAs targeted against HIV-1 rev transcripts in human cells," Nat. Biotechnol. 20(5):500-5.
Lewis et al. (2002) "Efficient delivery of siRNA for inhibition of gene expression in postnatal mice," Nat. Genet. 32(1):107-8.
Lim et al. (2003) "The microRNAs of Caenorhabditis elegans," Genes Dev. 17(8):991-1008.
Lim et al. (2003) "Vertebrate microRNA genes," Science. 299(5612):1540.
Liu et al. (1999) "Hydrodynamics-based transfection in animals by systemic administration of plasmid DNA," Gene Ther. 6:1258-1266.
McCaffrey et al. (2002) "RNA interference in adult mice," Nature. 418(6893):38-9.
McManus et al. (2002) "Small interfering RNA-mediated gene silencing in T lymphocytes," J. Immunol. 169(10):5754-60.
Miyagishi et al. (2002) "U6 promoter-driven siRNAs with four uridine 3' overhangs efficiently suppress targeted gene expression in mammalian cells," Nat. Biotechnol. 20:497-500.
Mourelatos et al. (2002) "miRNPs: a novel class of ribonucleoproteins containing numerous microRNAs," Genes Dev. 16(6):720-8.
Nielsen et al. (1991) "Sequence-selective recognition of DNA by strand displacement with a thymine-substituted polyamide," Science. 254(5037):1497-500.
Paddison et al. (2002) "RNA interference: the new somatic cell genetics?" Cancer Cell. 2(1):17-23.
Paddison et al. (2002) "Short hairpin RNAs (shRNAs) induce sequence-specific silencing in mammalian cells," Genes Dev. 16(8):948-58.
Paddison et al. (2002) "Stable suppression of gene expression by RNAi in mammalian cells," Proc. Natl. Acad. Sci. USA. 99(3):1443-8.
Pasquinelli et al. (2000) "Conservation of the sequence and temporal expression of let-7 heterochronic regulatory RNA," Nature. 408(6808):86-9.
Paul et al. (2002) "Effective expression of small interfering RNA in human cells," Nat. Biotechnol. 20(5):505-8.
Petersen et al. (2003) "LNA: a versatile tool for therapeutics and genomics," Trends Biotechnol 21:74-81.
Putnam (1996) "Antisense strategies and therapeutic applications," Am. J. Health Syst. Pharm. 53(2):151-160, erratum at Am. J. Health Syst. Pharm. 53(3):325.
Reinhart et al. (2002) "Small RNAs correspond to centromere heterochromatic repeats," Science. 297(5588):1831.
Rusckowski et al. (2000) "Biodistribution and metabolism of a mixed backbone oligonucleotide (GEM 231) following single and multiple dose administration in mice," Antisense Nucleic Acid Drug Dev. 10(5):333-45.
Schwab et al. (1994) "An approach for new anticancer drugs: oncogene-targeted antisense DNA," Ann. Oncol. 5(Suppl 4):55-8.
Stein et al. (1999) "Systemic and central nervous system correction of lysosomal storage in mucopolysaccharidosis type VII mice," J. Virol. 73:3424-3429.
Stein et al. (2001) "Inhibition of Vesivirus infections in mammalian tissue culture with antisense morpholino oligomers," Antisense Nucleic Acid Drug Dev. 11(5):317-25.
Sui et al. (2002) "A DNA vector-based RNAi technology to suppress gene expression in mammalian cells," Proc. Natl. Acad. Sci. USA. 99(8):5515-20.
Trehoux et al. (May 31, 2015) "Micro-RNAs miR-29a and miR-330-5p function as tumor suppressors by targeting the MUC1 mucin in pancreatic cancer cells," Biochim Biophys Acta. 1853(10 Pt A):2392-403.
Tuschl (2002) "Expanding small RNA interference," Nat. Biotechnol. 20(5):446-8.
Tuschl et al. (2002) "Small interfering RNAs: a revolutionary tool for the analysis of gene function and gene therapy," Mol. Interv. 2(3):158-67.
Vorobjev et al. (2001) "Nuclease resistance and RNase H sensitivity of oligonucleotides bridged by oligomethylenediol and oligoethylene glycol linkers," Antisense Nucleic Acid Drug Dev. 11(2):77-85.
Wright et al. (2005) "Identification of factors that contribute to recombinant AAV2 particle aggregation and methods to prevent its occurrence during vector purification and formulation," Molecular Therapy. 12:171-178.
Xia et al. (2002) "siRNA-mediated gene silencing in vitro and in vivo," Nature Biotechnol. 20(10):1006-10.
Yekta et al. (2004) "MicroRNA-directed cleavage of HOXB8 mRNA," Science. 304(5670):594-6.
Yu et al. (2002) "RNA interference by expression of short-interfering RNAs and hairpin RNAs in mammalian cells," Proc. Natl. Acad. Sci. USA. 99(9):6047-52.
Zeng et al. (2002) "Both natural and designed micro RNAs can inhibit the expression of cognate mRNAs when expressed in human cells," Mol. Cell. 9(6):1327-33.

(56) References Cited

OTHER PUBLICATIONS

Zang et al. (2011) "Several rAAV vectors efficiently cross the blood-brain barrier and transduce neurons and astrocytes in the neonatal mouse central nervous system," Mol. Ther. 19(8):1440-8.

* cited by examiner

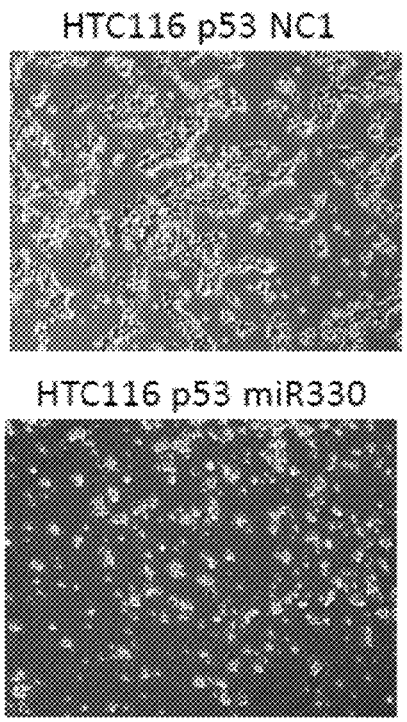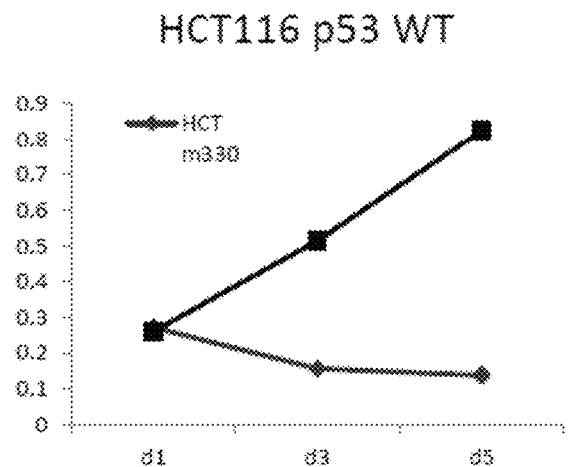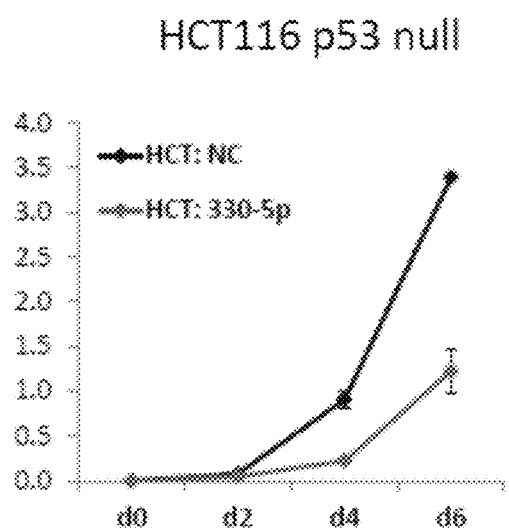
Fig. 4A
Fig. 4B

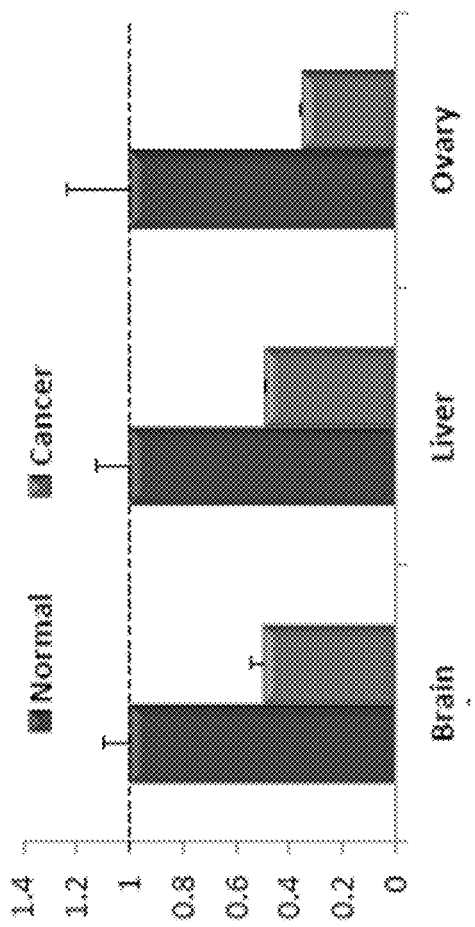
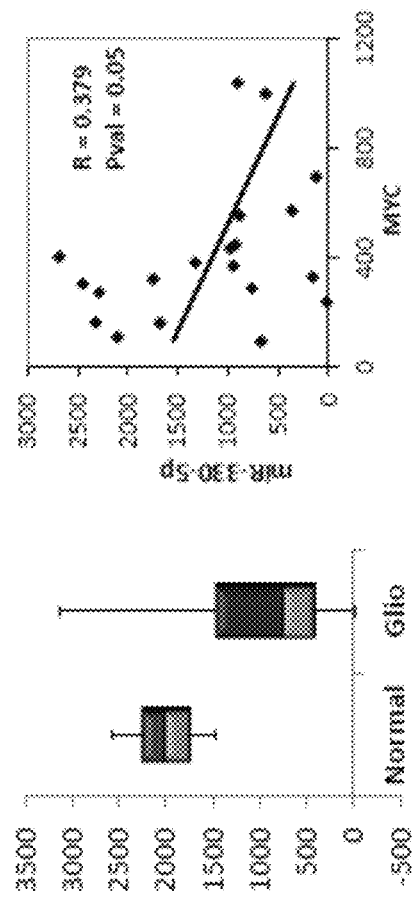
Fig. 5A
Fig. 5B
Fig. 5C

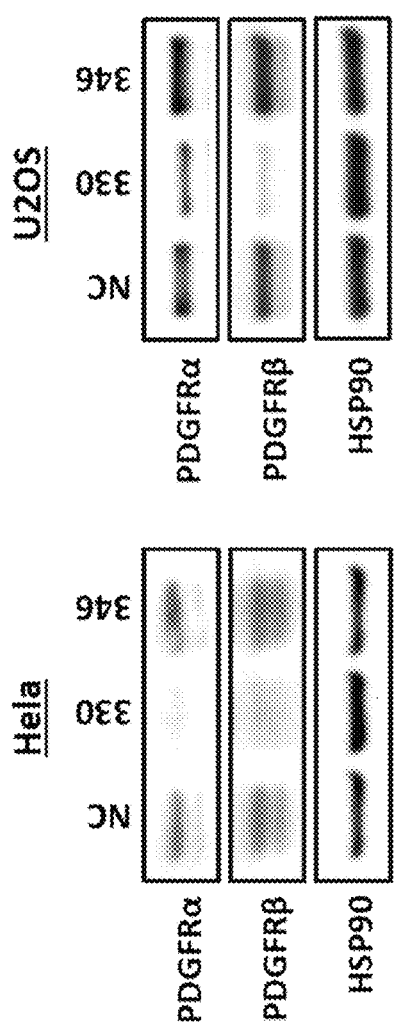

| Cancer Type | MYC status |
|---|---|
| Ovarian Cancer | 60-70% overexpression |
| Liver cancer | 50-100% overexpression |
| Melanoma | 40-90% overexpression |
| Breast Cancer | 20-50% amplification |
| Colon Cancer | 70% overexpression |
| Lung Cancer | 80-90% amplification |
| Uterine Cancer | 20% amplification |
| Prostate cancer | 30-60% amplification |

Fig. 7

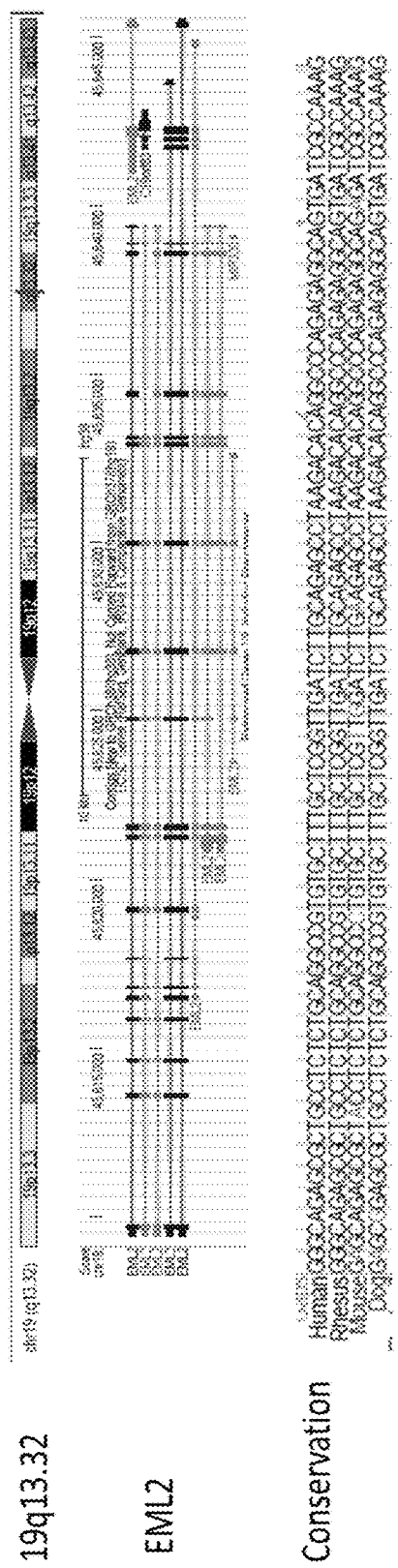
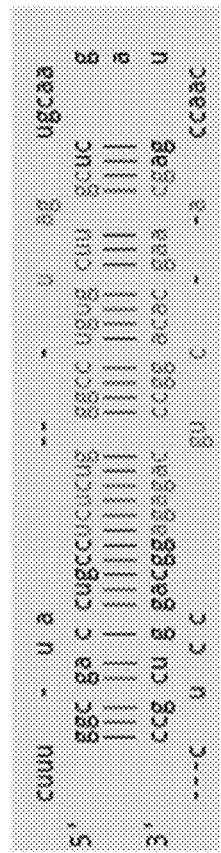
Fig. 8A
Fig. 8B

WT MRE  GGAGGAGACATGGTGAACCAGAGT

MUT MRE GGAGGAGACATGGTGAACCCCGT

NC+  330+  330+
NC   NC    TP

HSP90

MYC

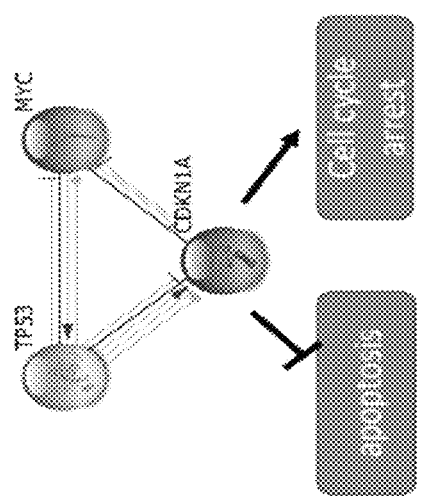
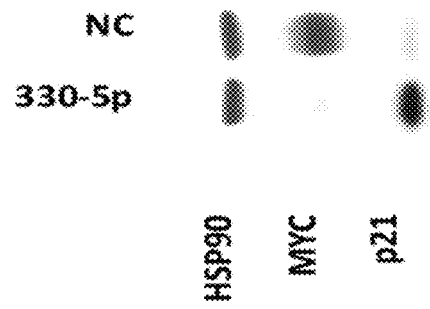
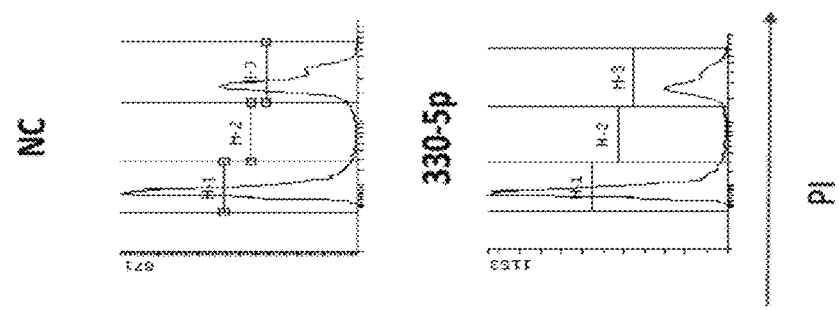
Fig. 10C
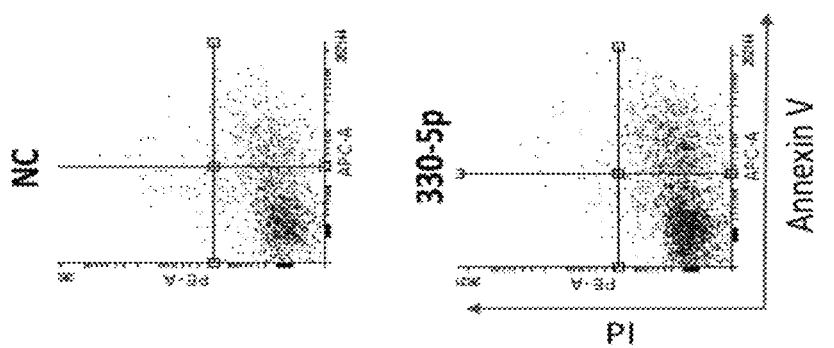
Fig. 10B
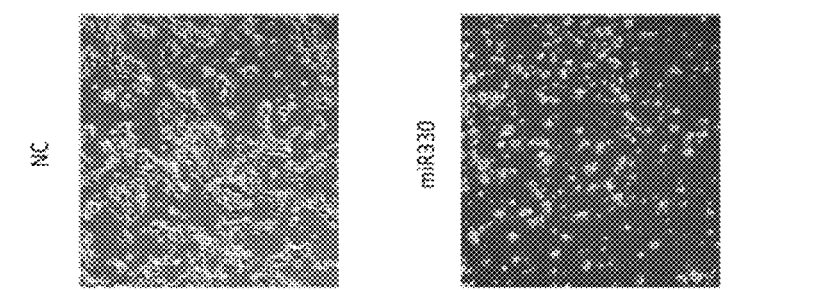
Fig. 10A

Fig. 25A

- HepG2 [Epithelial / HCC]
- SNU-475 [Epithelial / HCC]
- SNU-398 [Epithelial / HCC]
- SNU-449 [Epithelial / HCC]
- SNU-387 [Epithelial / HCC]
- SNU-423 [Epithelial / HCC]
- HepG2/C3A [Epithelial / HCC]
- Hep3B [Epithelial / HCC]
- Plc/prf/5 [Epithelial / Hepatoma]
- SK-Hep-1 [Epithelial / Adenocarcinoma]
- Huh7 [Epithelial / HCC]

- HEPA1-6 [Epithelial / Hepatoma MOUSE]

Fig. 25B

| System | Transgene | Promotor |
|---|---|---|
| Constitutive expression system | HBx | HBV |
| | HBx + pre C-C sequence | HBV |
| | p21 + HBsAg | HBV |
| | p21 + HBx | HBV |
| | HCV core, E1, E2 | HBV |
| Conditional expression system | HBV | albumin |
| | HCV core, E1, E2 | albumin |
| | c-myc | albumin |
| | c-myc + E2F1 | albumin |
| | TGF-α | metallothionein |
| | TGF-α + c-myc | albumin |
| | SV40 T-antigen | antithrombin III |
| Inducible expression system | myc | LAP |

Total body miR-330 knockout transgenic mouse

In vivo somatic mutation of mir-330

COMPOUNDS THAT TARGET MYC MICRORNA RESPONSIVE ELEMENTS FOR THE TREATMENT OF MYC-ASSOCIATED CANCER

RELATED APPLICATION

This application claims the benefit of U.S. Provisional Patent Application Ser. No. 62/438,303, filed Dec. 22, 2016, the entire disclosure of which is hereby incorporated herein by reference.

STATEMENT OF FEDERALLY SPONSORED RESEARCH

This invention was made with government support under Grant No. CA197529 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Feb. 14, 2018, is named 597627_BI9-003_SL.txt and is 7,895 bytes in size.

FIELD OF THE INVENTION

This disclosure relates to novel nucleic acid sequences that target one or more MYC microRNA (miR) Responsive Elements (MRE) in MYC-associated cancers.

BACKGROUND

The nuclear transcription factor c-MYC is a member of the MYC gene family having multiple functions and located on band q24.1 of chromosome 8. The c-MYC gene is activated by chromosomal translocation, rearrangement, and amplification. Its encoded protein transduces intracellular signals to the nucleus, resulting in the regulation of cell proliferation, differentiation, and apoptosis, and has the ability to transform cells and bind chromosomal DNA. c-MYC also plays a critical role in malignant transformation. The abnormal overexpression of c-MYC is frequently observed in some tumors, including carcinomas of the breast, colon, and cervix, as well as small-cell lung cancer, osteosarcomas, glioblastomas, and myeloid leukemias, therefore making it a possible target for anticancer therapy.

Although targeting the oncogenic effects of the c-MYC protein may have tremendous potential to treat cancer patients, drug development has been challenging for a variety of reasons. There are no drugs currently available that effectively target MYC-associated cancers. Although there are clinical trials underway to examine the efficacy of microRNA mimics in liver cancer and in hematological malignancies, these microRNAs are not known to target MYC.

SUMMARY

The present invention is based on the discovery that miR-330 is an extremely potent negative regulator of MYC over a wide spectrum of cancers, i.e., MYC-associated cancers. The present invention provides novel nucleic acid-based compounds such as, e.g., miR-330 mimic compounds and the like, to treat MYC-associated cancers.

Accordingly, in one aspect, a method of treating a MYC-associated cancer in a subject in need thereof is provided. The method comprises selecting a subject that overexpresses MYC, and administering to the subject a pharmaceutical composition comprising a nucleic acid sequence having at least 80% complementarity to a microRNA (miR) Responsive Element (MRE) sequence set forth as SEQ ID NO:1, thereby treating cancer in the subject.

In one embodiment, the nucleic acid sequence has at least 90%, at least 95% or at least 98% complementarity to the MRE sequence set forth as SEQ ID NO:1. In another embodiment, the nucleic acid sequence is further perfectly complementary to an MRE seed sequence set forth as SEQ ID NO:2. In another embodiment, the nucleic acid sequence is a double-stranded nucleic acid sequence having a sense strand and an antisense strand, wherein the antisense strand has at least 80% complementarity to the MRE sequence.

In another embodiment, the nucleic acid sequence comprises a miRNA, e.g., a miR-330 compound, or an siRNA. In another embodiment, the miRNA or siRNA is between 20 and 24 nucleotides in length.

In yet another embodiment, the MYC-associated cancer is further characterized by downregulation of hsa-miR-330-5p. In another embodiment, the MYC-associated cancer is liver cancer or colorectal cancer.

In yet another embodiment, the MRE is a MYC MRE. In another embodiment, MYC mRNA cleavage is mediated or translation of MYC mRNA is inhibited In another embodiment, MYC expression is downregulated in the subject after administering the pharmaceutical composition to the subject. In one embodiment, the nucleic acid sequence is administered using a recombinant Adeno-Associated virus (AAV).

In another aspect, a method of targeting MYC overexpression in a cancer cell characterized by overexpression of MYC, comprising contacting the cell with a nucleic acid sequence having at least 80% complementarity to an MRE sequence set forth as SEQ ID NO:1 to inhibit translation of the MYC mRNA is provided.

In one embodiment, the nucleic acid sequence comprises a miRNA (e.g., a miR-330 compound) or an siRNA.

In another aspect, an isolated nucleic acid comprising a sequence between 20 and 24 nucleotides in length having at least 80% complementarity to an MRE sequence set forth as SEQ ID NO:1 and comprising a modified nucleotide, is provided.

In one embodiment, the isolated nucleic acid sequence is further perfectly complementary to an MRE seed sequence set forth as SEQ ID NO:2. In another embodiment, the isolated nucleic acid sequence has at least 90%, at least 95% or at least 98% complementarity to the MRE sequence set forth as SEQ ID NO:1.

In one embodiment, the nucleic acid sequence comprises a miRNA (e.g., a miR-330 compound) or an siRNA.

In another aspect, a method of treating a MYC-associated cancer in a subject in need thereof, the method comprising selecting a subject that overexpresses MYC and administering to the subject a pharmaceutical composition comprising a modified miR-330 compound comprising SEQ ID NO:3, thereby treating cancer in the subject, is provided.

In another aspect, an isolated nucleic acid comprising a sequence between 20 and 24 nucleotides in length comprising at least 90% identity to SEQ ID NO:3, and comprising a modified nucleotide, wherein said nucleic acid sequence directs cleavage of MYC mRNA or inhibits translation of MYC mRNA, is provided.

In one embodiment, the isolated nucleic acid sequence of claim 28, comprises at least 95% identity to SEQ ID NO:3. In another embodiment, the isolated nucleic acid sequence comprises SEQ ID NO:3.

In another aspect, a miR-330-5p analogue comprising a nucleic acid sequence comprising at least 90% identity to SEQ ID NO:3, and having at least one modification selected from the group consisting of a deoxy-modified nucleotide, a locked nucleotide, an abasic nucleotide, an amino-modified nucleotide, an alkyl-modified nucleotide, a morpholino nucleotide, a phosphoramidate-modified nucleotide, a non-natural base-comprising nucleotide, an O-methyl modified nucleotide and a phosphorothioate is provided.

In one embodiment, the miR-330-5p analogue comprises at least 95% identity to SEQ ID NO:3. In another embodiment, the miR-330-5p analogue inhibits translation of MYC mRNA.

BRIEF DESCRIPTION OF THE DRAWINGS

FIG. 1A depicts a schematic of the human MYC transcript.

FIG. 1B depicts the location and sequence of the predicted microRNA response elements (MREs) for the respective microRNAs on the MYC transcript. Figure discloses SEQ ID NOS 7-11, 1, and 12-27, respectively, in order of appearance.

FIG. 1C depicts the effect of predicted MYC-targeting microRNAs on MYC protein expression in HeLa cells.

FIG. 2A depicts a schematic representation of MYC mRNA and MRE-889.

FIG. 2B depicts a luciferase assay that identifies MRE-889 in the MYC coding region as a direct target of miR-330 as assayed in HEK-293 cells.

FIG. 3A depicts that miR-330 overexpression leads to p21 overexpression in a p53-independent manner.

FIG. 3B depicts the results of FACS analysis of miR-330 overexpression which indicates perturbed cell proliferation as assayed in HCT116 colorectal carcinoma cells.

FIGS. 4A-4B show the effects of miR-330 overexpression.

FIG. 4A depicts representative HCT116 cells 72 hours post-transfection with mimic miR-330 (UCUCUGGGCCU-GUGUCUUAGGC, set forth as SEQ ID NO:6) or a control sequence.

FIG. 4B depicts growth curves of HCT116 cells following miR-330 overexpression.

FIGS. 5A-5c depict miR-330 expression levels in various tumors.

FIG. 5A depicts that miR-330 is downregulated in tumors of the brain, the liver, the ovary and the colon.

FIG. 5B depicts expression of miR-330 in normal and tumor glioma samples.

FIG. 5C depicts that miR-330 expression is significantly negatively correlated with MYC transcript expression.

FIGS. 6A-6B depict miR-330-5p regulation of Platelet-Derived Growth Factor Receptor (PDGFR).

FIG. 6A depicts the effect of miR-330 overexpression on PDGFRa and PDGFRb expression in HeLa cells and U-2 OS bone osteosarcoma cells.

FIG. 6B depicts the location and sequences of predicted MicroRNA Response Elements (MREs) for miR-330 on the PDGFRa and PDGFRb transcripts. Figure discloses SEQ ID NOS 28-36, respectively, in order of appearance.

FIG. 7 depicts a table showing MYC overexpression in multiple types of cancer.

FIGS. 8A-8B schematically depict hsa-miR-330.

FIG. 8A depicts the conservation of hsa-miR-330 among human, rhesus monkey, mouse and dog. Figure discloses SEQ ID NOS 37-40, respectively, in order of appearance.

FIG. 8B schematically depicts hsa-miR-330 prior to cleavage (i.e., the pre-miRNA). Figure discloses SEQ ID NO: 4.

FIG. 9A depicts a wild-type MYC MRE-889 sequence and a mutant MYC MRE-889 sequence. Figure discloses SEQ ID NOS 41-42, respectively, in order of appearance.

FIG. 9B depicts MRE-889 specific protector oligonucleotide recued endogenous MYC levels. Figure discloses SEQ ID NO: 43.

FIGS. 10A-10D depict hsa-miR-330 induction of p21 overexpression and cell cycle arrest.

FIG. 10A depicts the effect of has-miR330-5p up-regulation on clochard cells in vitro.

FIG. 10B depicts the effect of has-miR330-5p up-regulation on apoptosis.

FIG. 10C depicts the effect of has-miR330-5p up-regulation on cell cycle.

FIG. 10D depicts the effect of has-miR330-5p up-regulation on p21 expression.

FIG. 12A The effect of has-miR330-5p up-regulation on HCT116 p53 WT colorectal cancer cell line proliferation.

FIG. 12B The effect of has-miR330-5p up-regulation on HCT116 p53 NULL colorectal cancer cell line proliferation.

FIG. 12C depicts MYC and p21 levels following has-miR330-5p up-regulation in HCT116 p53WT/NULL.

FIG. 13A schematically depicts of p21 regulation by has-miR330-5p.

FIG. 13B depicts inducible MYC overexpression in HCT116 colorectal cancer cells.

FIG. 13C depicts MYC overexpression prevent has-miR330-5p induced p21 up-regulation.

FIG. 14A depicts p21 levels following different mimic miR330-5p transfection in HCT116 cells.

FIG. 14B depicts quantitative representation of p21 up-regulation following has-miR330-5p up-regulation.

FIG. 15A depicts the effect of has-miR330-5p up-regulation on proliferation of cervical cancer HeLa cells.

FIG. 15B depicts the effect of has-miR330-5p up-regulation on HeLa cells colony formation in soft agar.

FIG. 15C depicts quantitative representation of number and measurements of HeLa colonies in soft agar.

FIG. 21A depicts MYC amplification in HCC.

FIG. 21B depicts an increase in MYC mRNA levels in HCC.

FIG. 21C depicts a correlation between MYC amplification and poor survival in HCC patients.

FIGS. 25A-25B depict HCC cell lines and models for use according to certain aspects of the invention.

FIG. 25A depicts HCC cell lines.

FIG. 25B depicts genetically engineered mouse models for HCC.

FIG. 26A depicts a mouse having an in vivo somatic mutation of miR-330.

FIG. 26B a total-body miR-330 knockout transgenic mouse.

FIG. 29A depicts mutation efficiency of mouse miR330 locus by CRISPR=Cas9.

FIG. 29B depicts levels of mouse miR330-3p and miR330-5p in 3T3 cells following CRISPR-Cas9 mir330 knockout.

FIG. 29C depicts 3T3 cells proliferation following CRISPR-Cas9 mir330 knockout.

DETAILED DESCRIPTION OF CERTAIN EXEMPLARY EMBODIMENTS

Figures 1A, 1B:
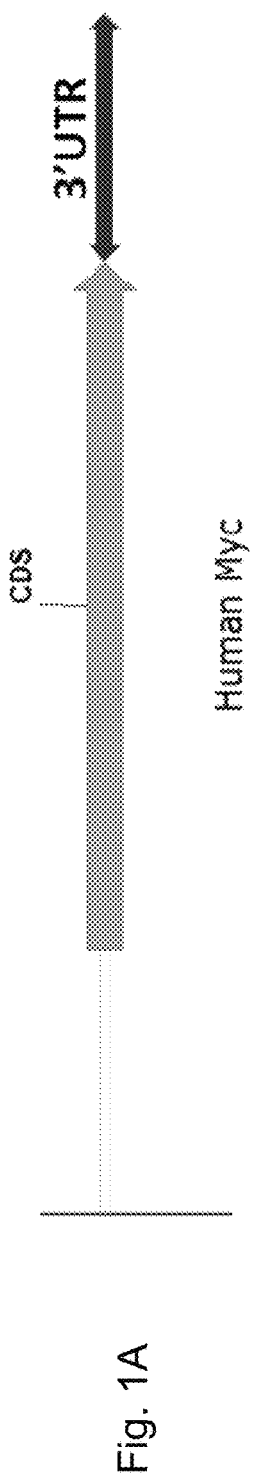
FIGS. 1A-1C show that miR-330 is a tumor suppressor targeting the MYC coding region.

Novel miR-330 nucleic acid sequences (e.g., modified miR-330-5p compounds, miR-330-5p analogue compounds, miR-330-5p siRNAs and the like and/or analogues and/or mutants thereof) that target one or more MYC MRE sequences are provided. Diagnostic and therapeutic methods using miR-330 nucleic acid sequences that target one or more MYC MRE sequences are provided. Reagents that target and downregulate MYC by binding to one or more MYC MRE sequences and/or or upregulate miR-330 are also provided.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

In certain embodiments, hsa-miR-330-5p downregulation is associated with a "MYC-associated cancer" or a "cancer characterized by overexpression of MYC," which refer to a cancer in a cell, tissue or organism that overexpresses MYC. Accordingly, certain embodiments of the invention are directed to the diagnosis and/or treatment of one or more MYC-associated cancers. By "treatment of MYC-associated cancer" or "treatment of a cancer characterized by overexpression of MYC" is meant the use of a nucleic acid sequence that mimics hsa-miR-330-5p and/or binds one or more MYC MREs to downregulate MYC expression, thus inhibiting a MYC-associated cancer or a cancer characterized by overexpression of MYC. In certain embodiments, the nucleic acid sequence binds one or more MYC MREs and mediates cleavage of an mRNA comprising one or more MYC MREs, i.e., a MYC mRNA. In other embodiments, the nucleic acid sequence binds one or more MYC MREs and prevents translation of an mRNA comprising one or more MYC MREs, i.e., a MYC mRNA.

The term "cancer" refers to various types of malignant neoplasms, most of which can invade surrounding tissues, and may metastasize to different sites (PDR Medical Dictionary 1st edition (1995)). The terms "neoplasm" and "tumor" refer to an abnormal tissue that grows by cellular proliferation more rapidly than normal and continues to grow after the stimuli that initiated proliferation is removed (PDR Medical Dictionary 1st edition (1995)). Such abnormal tissue shows partial or complete lack of structural organization and functional coordination with the normal tissue which may be either benign (i.e., benign tumor) or malignant (i.e., malignant tumor).

Cancers are classified by the type of cell that the tumor cells resemble, and is therefore presumed to be the origin of the tumor. These types include carcinomas, sarcomas, lymphomas and leukemias, germ cell tumors and blastomas. As used herein, a "carcinoma" refers to a cancer derived from epithelial cells. Carcinomas include many of the most common cancers, particularly in the aged, and include nearly all those developing in the breast, prostate, lung, pancreas, and colon. As used herein, a "sarcoma" refers to a cancer arising from connective tissue (e.g., bone, cartilage, fat, nerve), which develops from cells originating in mesenchymal cells outside the bone marrow. As used herein, "lymphoma" and "leukemia" refer to two classes of cancer that arise from hematopoietic cells in the marrow that typically to mature in the lymph nodes and blood, respectively. Leukemia is the most common type of cancer in children accounting for about 30%. As used herein a "germ cell tumor" refers to a cancer derived from pluripotent cells, most often presenting in the testicle or the ovary (seminoma and dysgerminoma, respectively). As used herein, a "blastomas" refers to a cancer derived from immature precursor cells or embryonic tissue. Blastomas are more common in children than in older adults.

"MYC-associated cancers" or "cancers characterized by overexpression of MYC" include, but are not limited to, ovarian cancer, liver cancer, melanoma, breast cancer, prostate cancer, glioma, lung and colorectal cancer. In particular embodiments, a MYC-associated cancer or a cancer characterized by overexpression of MYC is liver cancer or colorectal cancer.

By "therapeutic amount" is meant an amount that, when administered to a patient suffering from a MYC-associated cancer, is sufficient to cause a qualitative or quantitative reduction in the symptoms of a MYC-associated cancer, as described herein.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively), linear or circular. "mRNA" or "messenger RNA" is single-stranded RNA that specifies the amino acid sequence of one or more polypeptide chains. This information is translated during protein synthesis when ribosomes bind to the mRNA.

As used herein, the term "microRNA" ("miRNA"), also referred to in the art as "small temporal RNAs" ("stRNAs"), refers to a small (10-50 nucleotide) RNA (or nucleotide analogs) which can be genetically encoded (e.g., by viral, mammalian, or plant genomes) or synthetically produced and is capable of directing or mediating RNA silencing. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into an RNA-induced silencing complex (RISC), which recognizes target mRNAs through imperfect base pairing with the miRNA and most commonly results in translational inhibition or destabilization of the target mRNA.

As used herein, an "miRNA disorder" refers to a disease or disorder characterized by an aberrant expression or activity of an miRNA, e.g., a MYC-associated cancer.

In particularly preferred embodiments, an miRNA of the invention is miR-330. As used herein, the terms "miR-330" and "hsa-miR-330" are used interchangeably (unless stated otherwise) and refer to an miRNA that Applicants have discovered is able to regulate expression of MYC. miR-330 and hsa-miR-330 refer to both to the uncleaved form (i.e., the pre-miRNA form), as well as to the cleaved, mature forms, i.e., hsa-miR-330-5p (also referred to herein as "miR-330-5p") and hsa-miR-330-3p (also referred to herein as "miR-330-3p") of the miR-330 miRNA. The cleaved, mature forms of the miR-330 miRNA include the miRNA/miRNA duplex strands, as well as individual, uncomplexed stands of miR-330 miRNA.

miR-330 is also known as "MicroRNA 330," "EML2," "echinoderm microtubule-associated protein like 2," and "HuEMAP-2." The GeneCard ID for hsa-miR-330 is GC19M045607. The miRBase Accession Number for hsa-miR-330 is MI0000803. The sequence of the pre-miRNA form of hsa-miR-330 (i.e., the uncleaved form of miR-330), is set forth as 5'-CUUUGGCGAUCACUGCCUCU-CUGGGCCUGUGUCUUAGGCUCUGCAAGAUCA ACCGAGCAAAGCACACGGCCUGCAGAGAGGCA-GCGCUCUGCCC-3' (SEQ ID NO:4) and is shown in FIG. 8. The bold nucleotides represent the 5p and 3p sequences, respectively. The sequence of mature hsa-miR-330-5p is set forth as 5'-UCUCUGGGCCUGUGUCUUAGGC-3' (SEQ ID NO:3). The sequence of mature hsa-miR-330-3p is set forth as 5'-GCAAAGCACACGGCCUGCAGAGA-3' (SEQ ID NO:5).

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, an siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

As used herein, the term "short hairpin RNA" ("shRNA") (also known as "small hairpin RNAs") refers to an RNA (or RNA analog) including a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10 (4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10 (2):117-21, Rusckowski et al. Antisense Nucleic Acid Drug Dev. 2000 Oct. 10 (5):333-45, Stein, Antisense Nucleic Acid Drug Dev. 2001 Oct. 11 (5): 317-25, Vorobjev et al. Antisense Nucleic Acid Drug Dev. 2001 Apr. 11 (2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, pho sphorodiamidate, pho sphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to an inhibition of mRNA expression that typically includes selective intracellular degradation of RNA, but can also occur by inhibiting mRNA translation. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent having a strand which is "sufficiently complementary to a target RNA sequence to direct target-specific RNA interference (RNAi)" means that the strand has a sequence sufficient to trigger the destruction of the target RNA (e.g., target MRE) agent by the RNAi machinery or process or to inhibit translation of a target mRNA.

As used herein, the term "isolated RNA" (e.g., "isolated siRNA," "isolated siRNA precursor," "isolated miR precursor," "isolated miR" "isolated miR-5p" or "isolated miR-3p") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target polynucleotide sequence," e.g., when both polynucleotide sequences are present in the same cell. In certain embodiments, the target polynucleotide sequence corresponds to a target MYC MRE sequence, while the non-target polynucleotide sequence corresponds to a non-target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence. In preferred embodiments, a transgene encodes a miR-330 nucleic acid sequence (e.g., a modified miR-330-5p compound and/or a miR-330-5p analogue compound) and/or a MYC nucleic acid sequence and/or a complement thereof.

As used herein, "MRE sequence" and "MRE sequences" refer to MicroRNA Response Elements, which are sequences in mRNAs that are able to base pair with the 5p region of complementary miRNAs. Typically, MREs exhibit sequence conservation exclusively in a region termed a "seed sequence," while the remainder of the MRE sequence is diverse.

As used herein, "MYC MRE sequence" and "MYC MRE sequences" refer to MRE sequences found in MYC mRNA, e.g., human MYC mRNA. MYC MRE sequences of the invention that are specific to human MYC mRNA are depicted in FIG. 1B. In preferred embodiments, any of the four MYC MRE sequences as depicted in FIG. 1B corresponding to microRNA 330-5p are targeted by a modified miR-330-5p compound, a miR-330-5p analogue compound and/or a miR-330-5p siRNA compound of the present invention. In a particularly preferred embodiment, the MYC MRE sequence "MRE1 miR-330-5p" (also referred to herein as "MRE-889") set forth as 5'-AGGAGACATGGTGAACCA-GAGT-3' (SEQ ID NO:1) is targeted by a modified miR-330-5p compound, a miR-330-5p analogue compound and/or a miR-330-5p siRNA compound of the present invention (see FIG. 2). In another particularly preferred embodiment, the miR-330 MYC MRE seed sequence set forth as 5'-CCA-GAG-3' (SEQ ID NO:2) is targeted by a modified miR-330-5p compound, a miR-330-5p analogue compound and/or a miR-330-5p siRNA compound of the present invention.

As used herein, a "miR-330 agent" refers to a modified miR-330-5p compound, a miR-330-5p analogue compound and/or a miR-330-5p siRNA compound that binds to one or more target MYC MRE sequences ("MYC MREs"), and inhibits translation of a MYC mRNA, mediates cleavage of a MYC mRNA or otherwise suppresses expression of a MYC mRNA.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least one common MYC-associated cancer.

The phrase "examining the function of a miR-330 agent in a cell or organism" refers to examining or studying the expression, activity, function or phenotype arising therefrom.

As used herein an "animal model" refers to any non-human animals and biological samples derived therefrom that can be used to study a MYC-associated cancer. Animal models include non-human animals that express a MYC-associated cancer (e.g., animal models of cancer). Animal models also include non-human animals that overexpress MYC and/or underexpress miR-330. In certain embodiments, an animal that overexpresses MYC and/or underexpresses miR-330 exhibits one or more symptom of a MYC-associated cancer. Animal models also include non-human animals that express an exogenous miR-330 nucleic acid sequence (e.g., a modified miR-330-5p compound, a miR-330-5p analogue compound and/or a miR-330-5p siRNA compound). Animal models are useful for screening modulators, e.g., antagonists and/or agonists of one or more miR-330 and/or MYC activities. Exemplary animal models include, but are not limited to, mice, rats, hamsters, rabbits, dogs, cats, livestock, zebrafish and non-human primates.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, $^2$N-methylguano sine and $^{2,2}$N,N-dimethylguano sine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "dual functional oligonucleotide" refers to a miR-330 agent having the formula T-L-µ, wherein T is a MYC MRE targeting moiety, L is a linking moiety, and µ is a miRNA recruiting moiety. As used herein, the terms "MYC MRE targeting moiety," "targeting moiety," "MYC MRE targeting portion" or "targeting portion" refer to a domain, portion or region of the dual functional oligonucleotide having sufficient size and sufficient complementarity to a portion or region of a MYC MRE chosen or targeted for silencing (i.e., the moiety has a sequence sufficient to capture the target MYC MRE). As used herein, the term "linking moiety" or "linking portion" refers to a domain, portion or region of the RNA-silencing agent which covalently joins or links the miR-330 agent.

As used herein, the term "antisense strand," "first strand" or "5p strand" of a miR-330 agent (e.g., a MYC MRE inhibiting agent), e.g., an siRNA, an shRNA or a miRNA, refers to a strand that is substantially identical to a section of about 10-50 nucleotides, e.g., about 15-30, 16-25, 18-23 or 19-22 nucleotides of the miR-330-5p nucleic acid sequence or substantially complementary to a section of about 10-50 nucleotides, e.g., about 15-30, 16-25, 18-23 or 19-22 nucleotides of one or more MYC MREs and/or of the miR-330-3p nucleic acid sequence. The antisense strand, first strand or 5p has sequence sufficiently complementary to the desired target MYC MRE sequence to direct target-specific silencing, e.g., complementarity sufficient to trigger the destruction of the desired target one or more MYC MRE sequences by the RNAi machinery or process or complementarity sufficient to inhibit translation of an mRNA containing the one or more MYC MRE sequences.

The term "sense strand," "second strand" or "3p strand" of an RNA silencing agent, e.g., an siRNA, an shRNA or a miRNA, refers to a strand that is complementary to the antisense strand, first strand or 5p strand. Antisense and sense strands can also be referred to as first or second strands, the first or second strand having complementarity to the target sequence and the respective second or first strand having complementarity to said first or second strand. miRNA duplex intermediates, siRNA-like duplexes, include a miRNA strand having sufficient complementarity to a section of about 10-50 nucleotides of the MYC MRE targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target MYC MRE or a 5p strand of a pre-miRNA.

As used herein, the term "asymmetry," as in the asymmetry of the duplex region of an RNA silencing agent (e.g., the stem of an shRNA or a pre-miRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an antisense strand or a 5p strand, refers to the 5' terminal nucleotides, e.g., between one and about 5 nucleotides at the 5' terminus of the antisense strand. As used herein, the "3' end," as in the 3' end of a sense strand or a 3p strand, refers to the region, e.g., a region of between about one and about 5 nucleotides, that is complementary to the nucleotides of the 5' end of the complementary antisense strand or 5p strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of nucleic acid sequence that binds an MRE sequence and a target MRE sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprises a nitrogen-containing aromatic heterocyclic moiety.

As used herein, the terms "sufficient complementarity" or "sufficient degree of complementarity" can mean that a nucleic acid sequence that binds an MRE has a sequence which is sufficient to bind the desired target MRE and to trigger the RNA silencing of the target RNA (e.g., mRNA) containing the MRE. The terms "sufficient complementarity" or "sufficient degree of complementarity" can also mean that an antisense strand, first strand or 5p strand has a sequence which is sufficient to bind a complementary strand, i.e., a sense strand, a second strand or a 3p strand, respectively.

Various methodologies of the instant invention include a step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, splice rate, translation rate, biological activity, cellular characteristic or property, genotype, phenotype, etc. can be determined prior to introducing an MRE-inhibiting agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

I. Diagnostic and Prognostic Methods

The overexpression of MYC and/or downregulation of miR-330 can be correlated with the presence of one or more MYC-associated cancers (e.g., liver cancer, colorectal cancer, ovarian cancer, breast cancer, prostate cancer, melanoma and the like). In certain embodiments, a cell or an organism having a MYC-associated cancer has a downregulation of hsa-miR-330-5p. Accordingly, detecting or monitoring the presence of hsa-miR-330-5p are important diagnostic and prognostic tools, respectively, for detecting or monitoring progression of a MYC-associated cancer.

An exemplary method for detecting the presence or absence of hsa-miR-330-5p and/or MYC in a biological sample involves obtaining a biological sample from a test subject and contacting the biological sample with a compound or an agent capable of detecting hsa-miR-330-5p and/or MYC such that the presence of hsa-miR-330-5p and/or MYC is detected in the biological sample. A preferred agent for detecting hsa-miR-330-5p and/or MYC is a labeled nucleic acid probe capable of hybridizing to hsa-miR-330-5p and/or MYC. Other suitable probes for use in the diagnostic assays of the invention are described herein.

In one embodiment, the biological sample contains hsa-miR-330-5p and/or MYC from the test subject. A preferred biological sample is a serum sample or biopsy isolated by conventional means from a subject.

In another embodiment, the methods further involve obtaining a control biological sample from a control subject, contacting the control sample with a compound or agent capable of detecting hsa-miR-330-5p and/or MYC, such that the presence of hsa-miR-330-5p and/or MYC is detected in the biological sample, and comparing the presence of hsa-miR-330-5p and/or MYC in the control sample with the presence of hsa-miR-330-5p and/or MYC in the test sample.

The diagnostic methods described herein can furthermore be utilized to identify subjects having or at risk of developing a MYC-associated cancer associated with downregulated hsa-miR-330-5p expression and/or upregulated MYC expression.

The assays described herein, such as the preceding diagnostic assays or the following assays, can be utilized to identify a subject having or at risk of developing a MYC-associated cancer associated with downregulated hsa-miR-330-5p expression and/or upregulation of MYC. Thus, the present invention provides a method for identifying a MYC-associated cancer associated with downregulated hsa-miR-330-5p expression and/or upregulation of MYC or activity in which a test sample is obtained from a subject and hsa-miR-330-5p and/or upregulation of MYC is detected, wherein downregulation of hsa-miR-330-5p and/or upregulation of MYC is diagnostic for a subject having or at risk of developing a MYC-associated cancer. As used herein, a "test sample" refers to a biological sample obtained from a subject of interest. For example, a test sample can be a biological fluid (e.g., serum), cell sample or tissue sample (e.g., a biopsy).

Furthermore, prognostic assays described herein can be used to determine whether a subject can be administered an agent, e.g., a MYC MRE-binding agent (e.g., an agonist, antagonist, peptidomimetic, protein, peptide, nucleic acid, small molecule, RNAi agent or other drug candidate) to treat a MYC-associated cancer associated with hsa-miR-330-5p downregulation and/or upregulation of MYC. For example, such methods can be used to determine whether a subject can be effectively treated with an agent for cancer. Thus, the present invention provides methods for determining whether a subject can be effectively treated with an agent for a MYC-associated cancer associated with downregulated hsa-miR-330-5p and/or upregulated MYC expression or activity in which a test sample is obtained and hsa-miR-330-5p and/or MYC expression or activity is detected (e.g., wherein a decrease of hsa-miR-330-5p and/or an increase in MYC expression or activity is diagnostic for a subject that can be administered the agent to treat a MYC-associated cancer associated with downregulated hsa-miR-330-5p and/or upregulated MYC expression or activity).

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a MYC-associated cancer involving downregulated hsa-miR-330-5p and/or upregulated MYC expression or activity.

Furthermore, any fluid, tissue, cell or cell fraction in which hsa-miR-330-5p is expressed may be utilized in the prognostic assays described herein.

Monitoring the influence of miR-330 agents (e.g., drugs, e.g., RNAi agents) on the expression or activity of MYC can be applied not only in basic drug screening, but also in clinical trials. For example, the effectiveness of a miR-330 agent determined by a screening assay to decrease MYC expression or downregulate MYC activity, can be monitored in clinical trials of subjects exhibiting increased MYC expression and/or downregulated hsa-miR-330-5p expression or activity. In such clinical trials, the expression or activity of MYC can be used as a "read out" or markers of the phenotype of a particular cell.

For example, and not by way of limitation, MYC modulation in cells with downregulated hsa-miR-330-5p and/or upregulated MYC by treatment with a miR-330 agent (e.g., compound, drug or small molecule, e.g., an RNAi agent) which inhibits MYC expression and/or activity (e.g., identified in a screening assay as described herein) can be identified. Thus, to study the effect of miR-330 agents on MYC-associated cancer, for example, in a clinical trial, cells can be isolated and analyzed to determine the levels of expression of hsa-miR-330-5p and/or MYC and other markers implicated in the MYC-associated cancer. The levels of hsa-miR-330-5p and/or MYC expression (e.g., an hsa-miR-330-5p and/or MYC expression pattern) can be quantified by northern or western blot analysis or RT-PCR, using methods as described herein or known in the art, or by measuring the levels of activity of hsa-miR-330-5p and/or MYC. In this way, the hsa-miR-330-5p and/or MYC pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with a miR-330 agent (e.g., an agonist, antagonist, peptidomimetic, protein, peptide, nucleic acid, small molecule, RNAi agent or other drug candidate identified by the screening assays described herein) including the steps of (i) obtaining a pre-administration sample from a subject prior to administration of the agent; (ii) detecting the level of expression or activity of hsa-miR-330-5p and/or MYC in the pre-administration sample; (iii) obtaining one or more post-administration samples from the subject; (iv) detecting the level of expression or activity hsa-miR-330-5p and/or MYC in the post-administration samples; (v) comparing the level of expression or activity of hsa-miR-330-5p and/or MYC in the pre-administration sample with hsa-miR-330-5p and/or MYC in the post administration sample or samples; and (vi) altering the administration of the agent to the subject accordingly. For example, increased administration of the agent may be desirable to decrease the expression or activity of MYC to lower levels than detected, i.e., to increase the effectiveness of the miR-330 agent. Alternatively, decreased administration of the agent may be desirable to increase expression or activity of MYC to higher levels than detected, i.e., to decrease the effectiveness of the agent. According to such an embodiment, MYC expression or activity may be used as an indicator of the effectiveness of an agent, even in the absence of an observable phenotypic response.

II. Therapeutic Methods of Treatment

The present invention provides for both prophylactic and therapeutic methods of treating a subject at risk of (or susceptible to) a MYC-associated cancer mediated, in whole or in part, by upregulated MYC expression and/or downregulated miR-330 expression. In a preferred embodiment, the MYC-associated cancer is liver cancer or colorectal cancer.

"Treatment," or "treating," as used herein, is defined as the application or administration of a therapeutic agent, e.g., a miR-330 agent (e.g., an RNA agent or vector or transgene encoding same) to a patient, or application or administration of a therapeutic agent to an isolated tissue or cell line from a patient, who has a MYC-associated cancer, with the purpose to cure, heal, alleviate, relieve, alter, remedy, ameliorate, improve or affect the MYC-associated cancer, the symptoms of the MYC-associated cancer, or the predisposition toward MYC-associated cancer.

In one aspect, the invention provides a method for preventing in a subject a MYC-associated cancer by administering to the subject a therapeutic agent, e.g., an miR-330 agent (e.g., an RNAi agent or vector or transgene encoding the same). Subjects at risk for MYC-associated cancer can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods of treating subjects therapeutically, i.e., to alter onset of symptoms of MYC-associated cancer. In an exemplary embodiment, the modulatory method of the invention involves contacting a cell exhibiting downregulated hsa-miR-330-5p and/or upregulated MYC expression or activity with a therapeutic agent, e.g., a miR-330 agent (e.g., an RNAi agent or vector or transgene encoding the same) that is specific for one or more MYC MRE target sequences (e.g., one or more sequences set forth in FIG. 1 and/or fragments and/or homologs thereof), such that sequence specific interference with the MYC expression is achieved. These methods can be performed in vitro (e.g., by culturing the cell with the agent) or, alternatively, in vivo (e.g., by administering the agent to a subject).

Therapeutic agents, e.g., miR-330 agents, can be tested in an appropriate animal model in which the animal overexpresses MYC and/or exhibits downregulated hsa-miR-330-5p and/or upregulated MYC expression or activity. For example, a miR-330 agent (e.g., RNAi agent or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing a therapeutic agent, e.g., a miR330-5p agent (e.g., an RNAi agent) of the invention can be administered to any patient diagnosed as having or at risk for developing a MYC-associated cancer, such as cancer. In one embodiment, the patient is diagnosed as having a MYC-associated cancer, and the patient is otherwise in general good health. For example, the patient is not terminally ill, and the patient is likely to live at least two, three, five or more years following diagnosis. In another embodiment, the patient has not reached an advanced stage of the MYC-associated cancer. In another embodiment, the patient has reached an advanced stage of the MYC-associated cancer.

In one embodiment, a subject is administered an initial dose, and one or more maintenance doses of a therapeutic agent, e.g., a miR-330 agent (e.g., an RNAi agent). The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular MYC-associated cancer, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the MYC-associated cancer. The dosage of the compound may either be increased in the event the patient does not respond significantly to current dosage levels, or the dose may be decreased if an alleviation of the symptoms of the MYC-associated cancer is observed, if the MYC-associated has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of therapeutic agents (e.g., RNAi agents, cancer chemotherapeutics and the like). In another embodiment, the RNAi agents have sequences that are non-overlapping and non-adjacent to another species with respect to a naturally occurring target sequence. In another embodiment, the plurality of miR-330 agents is specific for different regions of a MYC MRE and/or for multiple MYC MREs. In another embodiment, the plurality of RNAi agents target two or more target MREs or regions of one or more target MREs (e.g., two, three, four, five, six, or more target MREs).

Following successful treatment, it may be desirable to have the patient undergo maintenance therapy to prevent the recurrence of the MYC-associated cancer, wherein the compound of the invention is administered in maintenance doses, ranging from 0.01 µg to 100 g per kg of body weight (see U.S. Pat. No. 6,107,094). In certain exemplary embodiments, maintenance therapy prevents a relapse from MYC-associated cancer remission in a subject.

The concentration of the therapeutic agent, e.g., a miR-330 agent (e.g., an RNAi agent), is an amount sufficient to be effective in treating or preventing a MYC-associated cancer in humans. The concentration or amount of therapeutic agent, e.g., a miR-330 agent (e.g., an RNAi agent) administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a therapeutic agent, e.g., a miR-330 agent (e.g., an RNAi agent) can include a single treatment or, preferably, can include a series of treatments. It will also be appreciated that the effective dosage of a therapeutic agent, e.g., a miR-330 agent (e.g., an RNAi agent) for treatment may increase or decrease over the course of a particular treatment. Changes in dosage may result and become apparent from the results of diagnostic assays as described herein. For example, the subject can be monitored after administering a therapeutic agent, e.g., a miR-330 agent (e.g., an RNAi agent). Based on information from the monitoring, an additional amount of the therapeutic agent, e.g., a miR-330 agent (e.g., an RNAi agent) can be administered.

Dosing is dependent on severity and responsiveness of the MYC-associated cancer to be treated, with the course of treatment lasting from several days to several months, or until a cure is effected or a diminution of the MYC-associated cancer is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a MYC-associated cancer, and/or downregulated hsa-miR-330-5p expression or activity.

III. Pharmaceutical Compositions and Methods of Administration

The invention pertains to uses of the above-described miR-330 agents for prophylactic and/or therapeutic treatments as described Infra. Accordingly, the miR-330 agent (e.g., RNAi agent) of the present invention can be incorporated into pharmaceutical compositions suitable for administration. Such compositions typically comprise the nucleic acid molecule or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds (e.g., one or more traditional chemotherapy compounds) can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The miR-330 agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The miR-330 agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the miR-330 agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of a miR-330-5p agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack or dispenser together with optional instructions for administration.

As defined herein, a therapeutically effective amount of a miR-330 agent, e.g., a RNAi agent (i.e., an effective dosage) depends on the RNAi agent. For instance, if a plasmid encoding shRNA or pre-miRNA is selected, single dose amounts in the range of approximately 1 µg to 1000 mg may be administered; in some embodiments, 10, 30, 100 or 1000 µg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The miR-330 agents (e.g., nucleic acid molecules) of the invention can be inserted into expression constructs, e.g., viral vectors, retroviral vectors, expression cassettes, or plasmid viral vectors, e.g., using methods known in the art, including but not limited to those described in Xia et al., (2002), Supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The miR-330 agents of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). Supra; Miyagishi and Taira (2002), Nature Biotechnol., 20, 497-500; Paddison et al. (2002), Supra; Paul (2002), Supra; Sui (2002) Supra; Yu et al. (2002), Supra.

The expression constructs may be any construct suitable for use in the appropriate expression system and include, but are not limited to, retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

The route of delivery can be dependent on the disorder of the patient. In certain exemplary embodiments, a subject diagnosed with a MYC-associated cancer, can be administered a miR-330 agent of the invention by IV or SC administration. In addition to a miR-330 agent of the invention, a patient can be administered a second therapy, e.g., a palliative therapy and/or MYC-associated cancer-specific therapy, e.g., one or more chemotherapeutic agents or cancer drugs known in the art. The secondary therapy can be, for example, symptomatic (e.g., for alleviating symptoms), protective (e.g., for slowing or halting disease progression), or restorative (e.g., for reversing the disease process).

In an exemplary embodiment, one or more miR-330 agents are used in combination with one or more known cancer drugs. For example, one or more miR-330 agents can be administered to a subject prior to treatment with one or more known cancer drugs, concomitant with treatment with one or more known cancer drugs, or after treatment with one or more cancer drugs. In certain embodiments, a miR-330 agent can potentiate the anti-cancer activity of one or more known cancer drugs.

In another exemplary embodiment, one or more miR-330 agents are used in combination with one or more known anti-MYC drugs. For example, one or more miR-330 agents can be administered to a subject prior to treatment with one or more known anti-MYC drugs, concomitant with treatment with one or more known anti-MYC drugs, or after treatment with one or more anti-MYC drugs. In certain embodiments, a miR-330 agent can potentiate the anti-cancer activity of one or more known anti-MYC drugs.

In an exemplary embodiment, one or more miR-330 agents are used to treat a subject having a cancer that is resistant to treatment with one or more cancer drugs known in the art. In other embodiments, a miR-330 agent is used during remission to prevent recurrence of the cancer from full remission. In other embodiments, a miR-330 agent is used to treat a cancer in partial remission.

In general, a miR-330 agent of the invention can be administered by any suitable method. As used herein, topical delivery can refer to the direct application of a miR-330 agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the miR-330 agent to the epidermis or dermis of a subject, or to specific strata thereof, or to an underlying tissue.

Compositions for intrathecal or intraventricular administration may include sterile aqueous solutions which may also contain buffers, diluents and other suitable additives. Compositions for intrathecal or intraventricular administration preferably do not include a transfection reagent or an additional lipophilic moiety besides, for example, the lipophilic moiety attached to the miR-330 agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

A miR-330 agent of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver drugs that may be readily formulated as dry powders. A miR-330 agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as Human Serum Albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffino se, maltodextrins, dextrans, and the like; alditols, such as mannitol, xylitol, and the like. A preferred group of carbohydrates includes lactose, trehalose, raffino se maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

A miR-330 agent of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, a miR-330 agent administered by oral or nasal delivery has been modified to be capable of traversing the blood-brain barrier.

In one embodiment, unit doses or measured doses of a composition that include a miR-330 agent are dispensed by an implanted device. The device can include a sensor that monitors a parameter within a subject. For example, the device can include a pump, such as an osmotic pump and, optionally, associated electronics.

A miR-330 agent can be packaged in a viral natural capsid or in a chemically or enzymatically produced artificial capsid or structure derived therefrom.

IV. Reagents

In certain exemplary embodiments, miR-330 agents of the invention (e.g., siRNAs, shRNAs or miRNAs) are designed to target a MYC MRE.

A. siRNA/miRNA Design

In some embodiments, siRNAs or miRNAs are designed as follows. First, at least a portion of the target (e.g., a MYC MRE) or at least a portion of a miR-330 pre-miRNA or a miR-330 miRNA is selected. Preferably, the target sequence (and corresponding sense strand) includes about 20 to 25 nucleotides, e.g., 20, 21, 22, 23, 24 or 25 nucleotides. More preferably, the portion (and corresponding sense strand) includes 21, 22 or 23 nucleotides. The skilled artisan will appreciate, however, that siRNAs or miRNAs having a length of less than 19 nucleotides or greater than 25 nucleotides can also function to mediate RNAi. Accordingly, siRNAs or miRNAs of such length are also within the scope of the instant invention provided that they retain the ability to mediate RNAi. Longer RNAi agents have been demonstrated to elicit an interferon or Protein Kinase R (PKR) response in certain mammalian cells which may be undesirable. Preferably, the RNAi agents of the invention do not elicit a PKR response (i.e., are of a sufficiently short length). However, longer RNAi agents may be useful, for example, in cell types incapable of generating a PRK response or in situations where the PKR response has been down-regulated or dampened by alternative means.

The sense strand sequence is designed such that the target sequence is essentially in the middle of the strand. Moving the target sequence to an off-center position may, in some instances, reduce efficiency of cleavage by the siRNA or miRNA. Such compositions, i.e., less efficient compositions, may be desirable for use if off-silencing of the MYC MRE is detected.

The antisense strand is routinely the same length as the sense strand and includes complementary nucleotides. In one embodiment, the strands are fully complementary, i.e., the strands are blunt-ended when aligned or annealed. In another embodiment, the strands comprise align or anneal such that 1-, 2- or 3-nucleotide overhangs are generated, i.e., the 3' end of the sense strand extends 1, 2 or 3 nucleotides further than the 5' end of the antisense strand and/or the 3' end of the antisense strand extends 1, 2 or 3 nucleotides further than the 5' end of the sense strand. Overhangs can comprise (or consist of) nucleotides corresponding to the target MYC MRE (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide comprises a nucleobase selected from the group consisting of 2-aminopurine and 2,6-diaminopurine.

To validate the effectiveness by which siRNAs or miRNAs destroy a MYC MRE-containing mRNA, the siRNA or miRNA can be incubated with a vector expressing circularizing exons in a *Drosophila*-based in vitro expression system. Radiolabeled with $^{32}$P, newly synthesized MYC mRNAs are detected autoradiographically on an agarose gel. The presence of cleaved MYC mRNAs indicates siRNA or miRNA efficacy. Suitable controls include omission of siRNA. Alternatively, control siRNAs or miRNAs are selected having the same nucleotide composition as the selected siRNA or miRNA, but without significant sequence complementarity to the appropriate target MYC MRE. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sites of siRNA-MYC MRE complementation are selected which result in optimal MYC MRE specificity and maximal MYC mRNA cleavage.

B. RNAi Agents

The present invention includes siRNA or miRNA molecules designed, for example, as described above. The siRNA or miRNA molecules of the invention can be chemically synthesized, or can be transcribed in vitro from a DNA template, or obtained in vivo from e.g., shRNA or miRNA, or by using recombinant human DICER enzyme, to cleave in vitro transcribed dsRNA templates into pools of 20-, 21- or 23-bp duplex RNA mediating RNAi. The siRNA or miRNA molecules can be designed using any method known in the art.

In one aspect, instead of the RNAi agent being an interfering ribonucleic acid, e.g., an siRNA or shRNA or miRNA as described above, the RNAi agent can encode an interfering ribonucleic acid, e.g., an shRNA or a pre-miRNA, as described above. In other words, the RNAi agent can be a transcriptional template of the interfering ribonucleic acid. Thus, RNAi agents of the present invention can also include shRNAs, and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, Supra; Paul et al., 2002, Supra; Sui et al., 2002 Supra; Yu et al., 2002, Supra. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of_PCR_strategy1.pdf).

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA or miRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs or miRNAs can be delivered into cells by methods known in the art, including cationic liposome transfection and electroporation. To obtain longer term suppression of the target MYC mRNA and to facilitate delivery under certain circumstances, one or more siRNAs can be expressed within cells from recombinant DNA constructs. Such methods for expressing siRNA or miRNA duplexes within cells from recombinant DNA constructs to allow longer-term target suppression in cells are known in the art, including mammalian Pol III promoter systems (e.g., H1 or U6/snRNA promoter systems (Tuschl, T., 2002, Supra) capable of expressing functional double-stranded siRNAs or miRNAs; (Bagella et al., 1998; Lee et al., 2002, Supra; Miyagishi et al., 2002, Supra; Paul et al., 2002, Supra; Yu et al., 2002), Supra; Sui et al., 2002, Supra). Transcriptional termination by RNA Pol III occurs at runs of four consecutive T residues in the DNA template, providing a mechanism to end the siRNA or miRNA transcript at a specific sequence. The siRNA or miRNA is complementary to the sequence of the target MYC MRE sequence in 5'-3' and 3'-5' orientations, and the two strands of the siRNA or miRNA can be expressed in the same construct or in separate constructs. Hairpin siRNAs or miRNA, driven by H1 or U6 snRNA promoter and expressed in cells, can inhibit target MYC mRNAs (Bagella et al., 1998; Lee et al., 2002, Supra; Miyagishi et al., 2002, Supra; Paul et al., 2002, Supra; Yu et al., 2002), Supra; Sui et al., 2002, Supra). Constructs containing siRNA or miRNA sequence under the control of T7 promoter also make functional siRNAs or miRNAs when cotransfected into the cells with a vector expressing T7 RNA polymerase (Jacque et al., 2002, Supra). A single construct may contain multiple sequences coding for siRNAs or miRNAs, such as multiple MYC MREs or a complement thereof, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to an MRE of a target MYC mRNA, a vector construct that expresses the engineered precursor can be used to produce siRNAs to initiate RNAi against specific MYC mRNA targets in mammalian cells (Zeng et al., 2002, supra). When expressed by DNA vectors containing polymerase III promoters, microRNA designed hairpins can silence gene expression (McManus et al., 2002, supra). MicroRNAs targeting polymorphisms may also be useful for blocking translation of mutant proteins, in the absence of siRNA- or miRNA-mediated gene-silencing. Such applications may be useful in situations, for example, where a designed siRNA or miRNA caused off-target silencing of wild type protein.

Viral-mediated delivery mechanisms can also be used to induce specific silencing of targeted MYC MREs through expression of siRNA or miRNA, for example, by generating recombinant adenoviruses harboring siRNA or miRNA under RNA Pol II promoter transcription control (Xia et al., 2002, supra). Infection of HeLa cells by these recombinant adenoviruses allows for diminished target MYC mRNA expression. Injection of the recombinant adenovirus vectors into transgenic mice expressing the target genes of the siRNA or miRNA results in in vivo reduction of target MYC mRNA expression. Id. In an animal model, whole-embryo electroporation can efficiently deliver synthetic siRNA or miRNA into post-implantation mouse embryos (Calegari et al., 2002). In adult mice, efficient delivery of siRNA or miRNA can be accomplished by "high-pressure" delivery technique, a rapid injection (within 5 seconds) of a large volume of siRNA or miRNA containing solution into animal via the tail vein (Liu et al., 1999, supra; McCaffrey et al., 2002, supra; Lewis et al., 2002. Nanoparticles and liposomes can also be used to deliver siRNA or miRNA into animals. In certain exemplary embodiments, recombinant adeno-associated viruses (rAAVs) and their associated vectors can be used to deliver one or more siRNAs or miRNAs into cells (US Patent Applications 2014/0296486, 2010/0186103, 2008/0269149, 2006/0078542 and 2005/0220766).

The nucleic acid compositions of the invention include both unmodified siRNAs or miRNAs and modified siRNAs or miRNAs as known in the art, such as crosslinked siRNA or miRNA derivatives or derivatives having non nucleotide moieties linked, for example to their 3' or 5' ends. Modifying siRNA or miRNA derivatives in this way may improve cellular uptake or enhance cellular targeting activities of the resulting siRNA or miRNA derivative as compared to the corresponding siRNA or miRNA, are useful for tracing the siRNA or miRNA derivative in the cell, or improve the stability of the siRNA or miRNA derivative compared to the corresponding siRNA or miRNA.

Engineered RNA precursors, introduced into cells or whole organisms as described herein, will lead to the production of a desired siRNA or miRNA molecule. Such an siRNA or miRNA molecule will then associate with endogenous protein components of the RNAi pathway to bind to and target a specific MYC MRE for cleavage and destruction. In this fashion, the MYC MRE-containing mRNA to be targeted by the siRNA or miRNA generated from the engineered RNA precursor will be depleted from the cell or organism, leading to a decrease in the concentration of the MYC protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA or miRNA can be radiolabeled, e.g., using $^3$H, $^{32}$P or other appropriate isotope.

Moreover, because RNAi is believed to progress via at least one single-stranded RNA intermediate, the skilled artisan will appreciate that ss-siRNAs or ss-miRNAs (e.g., the antisense strand or 5p strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

C. miR-330 Agents

The present invention features miR-330 agents (e.g., siRNA, shRNAs, pre-miRNAs and miRNAs), methods of making said RNA inhibiting agents, and methods (e.g., research and/or therapeutic methods) for using said improved RNA inhibiting agents (or portions thereof) for RNA inhibiting of one or more MYC mRNAs, e.g., by targeting one or more MYC MREs. The RNA inhibiting agents comprise an antisense strand (or portions thereof), wherein the antisense strand has sufficient complementary to a MYC MRE to mediate an RNA-mediated inhibition (e.g. RNAi).

a) Design of miR-330 shRNA Molecules

In certain featured embodiments, the instant invention provides shRNAs capable of mediating MYC mRNA inhibition (i.e., by binding to one or more MYC MRE sequences) with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post-transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNAs) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired miR-330 agents (e.g., siRNAs, shRNAs or miRNAs of the invention). By substituting one arm of the stem sequences of the pre-miRNA with sequence complementary to the target MYC MRE sequence, a shRNA is formed. The shRNA is processed by the entire gene silencing pathway of the cell, thereby efficiently mediating RNAi.

In the shRNAs (or engineered precursor RNAs) of the instant invention, one portion of the duplex stem is a nucleic acid sequence that is complementary (e.g., perfectly complementary or substantially complementary, e.g., anti-sense) to the MYC MRE target sequence and/or to miR-330-3p. Preferably, one strand of the stem portion of the shRNA is sufficiently complementary (e.g., antisense) to a target RNA (e.g., a MYC mRNA MRE sequence) or sufficiently homologous to miR-330-5p to mediate degradation or cleavage of said target RNA via RNA interference (RNAi). Alternatively, one strand of the stem portion of the shRNA is sufficiently complementary (e.g., antisense) to a target RNA (e.g., a MYC mRNA MRE sequence) or sufficiently homologous to miR-330-5p to inhibit translation of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target MYC mRNA (up to, including and larger than an entire MYC MRE sequence) and optionally including non-MRE MYC sequence.

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired miRNA or siRNA molecule described herein. In other embodiments, the sequence of the antisense portion of a shRNA can be designed essentially as described above or generally by selecting an 18, 19, 20, 21 nucleotide, or longer, sequence from within the target RNA (e.g., an MYC MRE sequence). In general, the sequence can be selected from any portion of the target RNA (e.g., MYC MRE sequence) including an intronic region, the 5' UTR (untranslated region), coding sequence, or 3' UTR, provided said portion is distant from the site of the gain-of-function mutation. In a particularly preferred embodiment, the sequence is an MRE in the coding sequence of MYC mRNA. This sequence can optionally follow immediately after a region of the target MRE containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of a MYC MRE target (or to miR-330-3p) wherein expression of the mRNA containing the target is to be reduced or inhibited. The two 3' nucleotides flanking this region of the stem are chosen so as to maximize the production of the siRNA or miRNA from the engineered RNA precursor and to maximize the efficacy of the resulting siRNA or miRNA in targeting the corresponding MYC mRNA for destruction by RNAi or in targeting the corresponding MYC mRNA to inhibit translation of the MYC mRNA in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nucl. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. miRscan or miRseeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila* melanogaster, Caenorhabditis elegans, zebrafish, Arabidopsis thalania, Mus musculus, and Rattus norvegicus as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNases (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism.

b) Design of miR-330 siRNA/miRNA Molecules

An siRNA molecule of the invention is a duplex consisting of a sense strand and complementary antisense strand, the antisense strand having sufficient complementary to a MYC MRE sequence to mediate RNAi. An miRNA molecule of the invention is optionally a duplex consisting of a 3p strand and complementary 5p strand, the 5p strand having sufficient complementary to a MYC MRE sequence to mediate RNAi. Preferably, the siRNA or miRNA molecule has a length from about 10-50 or more nucleotides, i.e., each strand comprises 10-50 nucleotides (or nucleotide analogs). More preferably, the siRNA or miRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA or miRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, siRNAs or miRNAs can be designed by using any method known in the art, for instance, by using the following protocol:

1. The siRNA or miRNA should be specific for a target sequence, e.g., a target sequence set forth in a MYC mRNA (e.g., a MYC MRE sequence). The first strand should be complementary to the target sequence, and the other strand should be substantially complementary to the first strand. In one embodiment, the target sequence is substantially complementary to a miR-330 sequence. A sense strand or 3p strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the siRNA or the 3p strand of the miRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs or miRNAs having a length of less than 19 nucleotides or greater than 25 nucleotides can also function to mediate RNAi. Accordingly, siRNAs or miRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. Preferably the RNA silencing agents of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The siRNA or miRNA molecules of the invention have sufficient complementarity with the target sequence such that the siRNA or miRNA can mediate RNAi. In general, siRNA- or miRNA-containing nucleotide sequences sufficiently identical to a target sequence portion of MYC mRNA (e.g., a MYC MRE sequence) to effect RISC-mediated cleavage of the target MYC mRNA are preferred. Accordingly, in a preferred embodiment, the sense strand of the siRNA is designed have to have a sequence sufficiently identical to a portion of the target (e.g., a MYC MRE sequence). For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair from the sense strand. Moreover, siRNA or miRNA sequences with small insertions or deletions of 1 or 2 nucleotides may also be effective for mediating RNAi. Alternatively, siRNA or miRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA or the 5p strand of the miRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target MYC MRE sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA or miRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature ($T_M$) of the hybrid, where $T_M$ is determined according to the following equations. For hybrids less than 18 base pairs in length, $T_M$ (° C.)=2(# of A+T bases)+4(# of G+C bases). For hybrids between 18 and 49 base pairs in length, $T_M$ (° C.)=81.5+16.6 (log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs or miRNAs should have the same nucleotide composition as the selected siRNA or miRNA, but without significant sequence complementarity to the appropriate genome. Such negative controls may be designed by randomly scrambling the nucleotide sequence of the selected siRNA or miRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs or miRNAs destroy target RNAs or downregulate translation (e.g., MYC MRE-containing mRNA), the siRNA or miRNA may be incubated with target cDNA (e.g., MYC cDNA) in a Drosophila-based in vitro MYC mRNA expression system. Radiolabeled with $^{32}P$, newly synthesized target RNAs (e.g., MYC MRE-containing mRNAs) are detected autoradiographically on an agarose or polyacrylamide gel. The presence of cleaved target RNA indicates RNA nuclease activity. Suitable controls include omission of siRNA or miRNA and use of non-target MYC MRE-containing mRNA. Alternatively, control siRNAs or miRNAs are selected having the same nucleotide composition as the selected siRNA or miRNA, but without significant sequence complementarity to the appropriate target gene. Such negative controls can be designed by randomly scrambling the nucleotide sequence of the selected siRNA or miRNA. A homology search can be performed to ensure that the negative control lacks homology to any other gene in the appropriate genome. In addition, negative control siRNAs or miRNAs can be designed by introducing one or more base mismatches into the sequence.

Anti-MYC MRE-containing mRNA siRNAs or miRNAs may be designed to target any of the target sequences described supra. Said siRNAs or miRNAs comprise an antisense strand which is sufficiently complementary with the target sequence to mediate silencing of the target sequence.

Sites of siRNA- or miRNA-MYC MRE complementation are selected which result in optimal MYC MRE specificity and maximal MYC mRNA cleavage and/or translational inhibition.

c) Dual Functional Oligonucleotide Tethers

In other embodiments, a miR-330 agent of the present invention includes dual functional oligonucleotide tethers useful for the intercellular recruitment of an miRNA. Animal cells express a range of miRNAs, noncoding RNAs of approximately 22 nucleotides which can regulate gene expression at the post transcriptional or translational level. By binding a miRNA bound to RISC and recruiting it to a target MYC MRE sequence, a dual functional oligonucleotide tether can repress the expression of genes involved e.g., in the arteriosclerotic process. The use of oligonucleotide tethers offer several advantages over existing techniques to repress the expression of a particular gene. First, the methods described herein allow an endogenous molecule (often present in abundance), an miRNA, to mediate RNA silencing. Accordingly, the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific MYC MRE sequences and specific miRNAs. The designs can be cell and gene product specific. As a result, these methods of RNA silencing are highly regulatable.

The dual functional oligonucleotide tethers ("tethers") of the invention are designed such that they recruit miRNAs (e.g., endogenous cellular miRNAs) to a target MYC MRE sequence so as to inhibit the MYC mRNA. In preferred embodiments, the tethers have the formula T-L-µ, wherein T is an MYC MRE sequence targeting moiety, L is a linking moiety, and µ is an miRNA recruiting moiety. Any one or more moiety may be double-stranded. Preferably, however, each moiety is single-stranded.

Moieties within the tethers can be arranged or linked (in the 5' to 3' direction) as depicted in the formula T-L-µ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: µ-T-L (i.e., the 3' end of the miRNA recruiting moiety linked to the 5' end of the linking moiety and the 3' end of the linking moiety linked to the 5' end of the targeting moiety).

The targeting moiety, as described above, is capable of capturing a specific target MYC MRE sequence. The targeting moiety should be of sufficient size to effectively bind the target MYC MRE sequence. The length of the targeting moiety will vary greatly depending, in part, on the length of the target MYC MRE sequence and the degree of complementarity between the target MYC MRE sequence and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The recruiting moiety, as described above, is capable of associating with an miRNA. According to the invention, the miRNA may be any miRNA capable of repressing the target MYC mRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

D. Modified miR-330 Agents

In certain aspects of the invention, a miR-330 agent (or any portion thereof) of the invention as described supra may be modified such that the activity of the agent is further improved. For example, a miR-330 agent described in herein may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

In certain embodiments, siRNA or miRNA compounds are provided having one or any combination of the following properties: (1) fully chemically-stabilized (i.e., no unmodified 2'-OH residues); (2) asymmetry; (3) 11-16 base pair duplexes; (4) alternating pattern of chemically-modified nucleotides (e.g., 2'-fluoro and 2'-methoxy modifications); and (5) single-stranded, fully phosphorothioated tails of 5-8 bases. In certain embodiments, the siRNA or miRNA compounds described herein can be conjugated to a variety of targeting agents, including, but not limited to, cholesterol, DHA, phenyltropanes, cortisol, vitamin A, vitamin D, Gal-Nac, and gangliozides.

1) Modifications to Enhance Target Discrimination

In certain embodiments, a miR-330 agent of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the miR-330 agent for a non-target MYC MRE sequence, without appreciably affecting the specificity of the miR-330 agent for a target MYC MRE sequence.

In preferred embodiments, the miR-330 agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target MYC MRE sequence. Exemplary universal nucleotide include those having an inosine base portion or an inosine analog base portion selected from the group consisting of deoxyinosine (e.g. 2'-deoxyino sine), 7-deaza-2'-deoxyino sine, 2'-aza-2'-deoxyino sine, PNA-inosine, morpholine-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the miR-330 agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In miR-330 agents having two strands or strand portions (e.g. siRNAs, shRNAs, miRNA duplexes), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the miR-330 agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention, an siRNA produced from a shRNA or a miRNA produced from a pre-miRNA) into RISC in favor of the sense strand, such that the antisense strand preferentially guides cleavage of a target MYC mRNA, and thus increasing or improving the efficiency of target cleavage and silencing. Preferably, the asymmetry of a miR-330 agent is enhanced by lessening the base pair strength between the antisense strand 5' end (AS 5') and the sense strand 3' end (S 3') of the miR-330 agent relative to the bond strength or base pair strength between the antisense strand 3' end (AS 3') and the sense strand 5' end (S '5) of said miR-330 agent.

In one embodiment, the asymmetry of a miR-330 agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of a miR-330 agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of a miR-330 agent of the invention may be enhanced such that there is at least one wobble base pair, e.g., G:U, between the 5' end of the first or antisense strand and the 3' end of the sense strand portion. In another embodiment, the asymmetry of a miR-330 agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of a miR-330 agent of the invention may be enhanced such that there is at least one base pair comprising a modified nucleotide. In preferred embodiments, the modified nucleotide comprises a nucleobase selected from the group consisting of 2-aminopurine and 2,6-diaminopurine.

3) miR-330 Agents with Enhanced Stability

The miR-330 agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features miR-330 agents that include first and second strands wherein the second strand and/or first strand is modified by the substitution of internal nucleotides with modified nucleotides, such that in vivo stability is enhanced as compared to a corresponding unmodified miR-330 agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention, the miR-330 agents may contain at least one modified nucleotide analogue. The one or more nucleotide analogues may be located at positions where the target-specific silencing activity, e.g., the RNAi mediating activity is not substantially effected, e.g., in a region at the 5'-end and/or the 3'-end of the siRNA or miRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moieties of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the miR-330 agent of the invention comprises Locked Nucleic Acids (LNAs). LNAs comprise sugar-modified nucleotides that resist nuclease activities (are highly stable) and possess single nucleotide discrimination for a MYC MRE sequence (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O, 4'-C-ethylene-bridged nucleic acids, with possible modifications such as 2'-deoxy-2''-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the miR-330 agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the miR-330 agent, for example, to increase half-life in the body. Thus, the invention includes miR-330 agents having two complementary strands of nucleic acid, wherein the two strands are cross-linked. The invention also includes miR-330 agents which are conjugated or unconjugated (e.g., at its 3' terminus) to another moiety (e.g. a non-nucleic acid moiety such as a peptide), an organic compound (e.g., a dye), or the like). Modifying siRNA or miRNA derivatives in this way may improve cellular uptake or enhance cellular targeting activities of the resulting siRNA or miRNA derivative as compared to the corresponding siRNA or miRNA, are useful for tracing the siRNA or miRNA derivative in the cell, or improve the stability of the siRNA or miRNA derivative compared to the corresponding siRNA or miRNA.

Other exemplary modifications include: (a) 2' modification, e.g., provision of a 2' OMe moiety on a U in a sense or antisense strand, but especially on a sense strand, and/or a 2' F moiety on a U in a sense or antisense strand, but especially on a sense strand, and/or a 2' OMe moiety in a 3' overhang, e.g., at the 3' terminus (3' terminus means at the 3' atom of the molecule or at the most 3' moiety, e.g., the most 3' P or 2' position, as indicated by the context) and/or a 2' F moiety; (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, miR-330 agents may be modified with chemical moieties, for example, to enhance cellular uptake by target cells (e.g., neuronal cells). Thus, the invention includes miR-330 agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, a miR-330 agent of invention is conjugated to a lipophilic moiety. In one embodiment, the lipophilic moiety is a ligand that includes a cationic group. In another embodiment, the lipophilic moiety is attached to one or both strands of an siRNA or an miRNA. In an exemplary embodiment, the lipophilic moiety is attached to one end of the sense strand of the siRNA or the 3p strand of the miRNA. In another exemplary embodiment, the lipophilic moiety is attached to the 3' end of the sense strand or the 3p strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

5) Tethered Ligands

Other entities can be tethered to a miR-330 agent of the invention. For example, a ligand tethered to a miR-330 agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of a miR-330 agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target MYC mRNA inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a miR-330 agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause a miR-330 agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to a miR-330 agent. In a guanidinoglycoside, the amine group on the amino acid is exchanged for a guanidine group. Attachment of a guanidine analog can enhance cell permeability of a miR-330 agent. A tethered ligand can be a poly-arginine peptide, peptide or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of a miR-330 agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified miR-330 agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a placental cell, a kidney cell and/or a liver cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g., cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the miR-330 agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the miR-330 agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue. For example, the target tissue can be the placenta, the kidneys or the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the placenta, liver and/or kidney and therefore less likely to be cleared from the body. A lipid or lipid-based ligand that binds to HSA less strongly can be used to target the conjugate to the placenta, liver and/or kidney. Other moieties that target to placental, liver and/or kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the fmiR-330 agent, such as by enhancing cellular recognition and absorption. The peptide or peptidomimetic moiety can be about 5-50 amino acids long, e.g., about 5, 10, 15, 20, 25, 30, 35, 40, 45 or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to a miR-330 agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

V. Methods of Introducing Nucleic Acids, Vectors and Host Cells miR-330 agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

miR-330 agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or other-wise increase inhibition of the target gene.

Physical methods of introducing nucleic acids include injection of a solution containing a miR-330 agent, bombardment by particles covered by the miR-330 agent, soaking the cell or organism in a solution of the miR-330 agent, or electroporation of cell membranes in the presence of the miR-330 agent. A viral construct packaged into a viral particle would accomplish both efficient introduction of an expression construct into the cell and transcription of miR-330 agent encoded by the expression construct. Other methods known in the art for introducing nucleic acids to cells may be used, such as lipid-mediated carrier transport, chemical-mediated transport, such as calcium phosphate, and the like. Thus the miR-330 agent may be introduced along with components that perform one or more of the following activities: enhance miR-330 agent uptake by the cell, inhibit annealing of single strands, stabilize the single strands, or otherwise increase inhibition of the target gene.

A miR-330 agent may be directly introduced into the cell (i.e., intracellularly); or introduced extracellularly into a cavity, interstitial space, into the circulation of an organism, introduced orally, or may be introduced by bathing a cell or organism in a solution containing the miR-330 agent. Vascular or extravascular circulation, the blood or lymph system, and the cerebrospinal fluid are sites where the miR-330 agent may be introduced.

The cell having the MYC MRE may be from the germ line or somatic, totipotent or pluripotent, dividing or non-dividing, parenchyma or epithelium, immortalized or transformed, or the like. The cell may be a stem cell or a differentiated cell. Cell types that are differentiated include, but are not limited to, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, cells of the endocrine or exocrine glands and the like.

Depending on the particular target MYC MRE and the dose of miR-330 agent delivered, this process may provide partial or complete elimination of the presence of aberrantly expressed MYC mRNA and/or MYC protein. A reduction or loss of MYC mRNA and/or MYC protein in at least 50%, 60%, 70%, 80%, 90%, 95% or 99% or more of targeted cells is exemplary. Inhibition of MYC refers to the absence (or observable decrease) in MYC mRNA and/or MYC protein levels or one or more MYC activities. Specificity refers to the ability to inhibit the MYC mRNA without manifesting effects on other RNA species (e.g., mRNA) of the cell. The consequences of inhibition can be confirmed by examination of the outward properties of the cell or organism (as presented below in the examples) or by biochemical techniques such as RNA solution hybridization, nuclease protection, northern hybridization, reverse transcription, gene expression monitoring with a microarray, antibody binding, Enzyme Linked ImmunoSorbent Assay (ELISA), western blotting, immunoprecipitation, RadioImmunoAssay (RIA), other immunoassays, and Fluorescence Activated Cell Sorting (FACS).

The miR-330 agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of a miR-330 agent of the invention is tested for its ability to specifically degrade, prevent translation of or otherwise downregulate MYC mRNA in cells. Readily transfectable cells suitable for cell-based validation assays include, for example, trophoblast cells, HeLa cells or COS cells. Cells are transfected with a vector expressing MYC mRNA or a complement thereof as described further herein. Standard siRNA or miRNA, modified siRNA or miRNA, or vectors able to produce siRNA or miRNA from U-looped mRNA or siRNA, respectively, are co-transfected. Selective reduction in target MYC mRNA expression or translation is measured. Reduction of target MYC mRNA expression or translation can be compared to levels of MYC mRNA expression or translation in the absence of a miR-330 agent or in the presence of an inhibiting agent that does not target MYC mRNA. Exogenously-introduced MYC mRNA can be assayed for comparison purposes.

Recombinant Adeno-Associated Viruses and Vectors

In certain exemplary embodiments, recombinant adeno-associated viruses (rAAVs) and their associated vectors can be used to deliver one or more miR-330 agents (e.g., siRNAs, shRNAs and/or miRNAs) into cells. AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In particular embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) Mol. Ther. 19(8):1440-8. doi: 10.1038/mt.2011.98. Epub 2011 May 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., baboon) or the like. In certain embodiments, a host animal is a non-human host animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the placenta, liver and/or kidneys of a subject. Recombinant AAVs may be delivered directly to the placenta, liver and/or kidney with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the invention may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

VI. Kits

In certain aspects, the invention provides kits that include a suitable container containing a pharmaceutical formulation of a miR-330 agent, e.g., a double-stranded or single-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain aspects, the invention provides kits that include a suitable container containing a nucleic acid sequence encoding a miR-330 agent. In certain embodiments the individual components of the pharmaceutical formulation may be provided in one container. Alternatively, it may be desirable to provide the components of the pharmaceutical formulation separately in two or more containers, e.g., one container for a miR-330 agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

In certain aspects, the invention provides kits that include a suitable container containing a nucleic acid sequence (e.g., an expression vector) encoding a miR-330 agent or a complement thereof and optional reagents for use with the vector. In certain embodiments, the individual components of the kit may be provided in one container. Alternatively, it may be desirable to provide the components of the kit separately in two or more containers, e.g., one container for an expression vector, and at least another for a buffer and/or other reagents. The kit may be packaged in a number of different configurations such as one or more containers in a single box. The different components can be combined, e.g., according to instructions provided with the kit. The components can be combined according to a method described herein, e.g., to express a miR-330 agent or complement thereof from an expression vector. The kit can also include a delivery vehicle (e.g., one or more transfection reagents).

EXAMPLES

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

Example I miR-330 is a Tumor Suppressor Targeting the MYC Coding Region

Figure 1C:
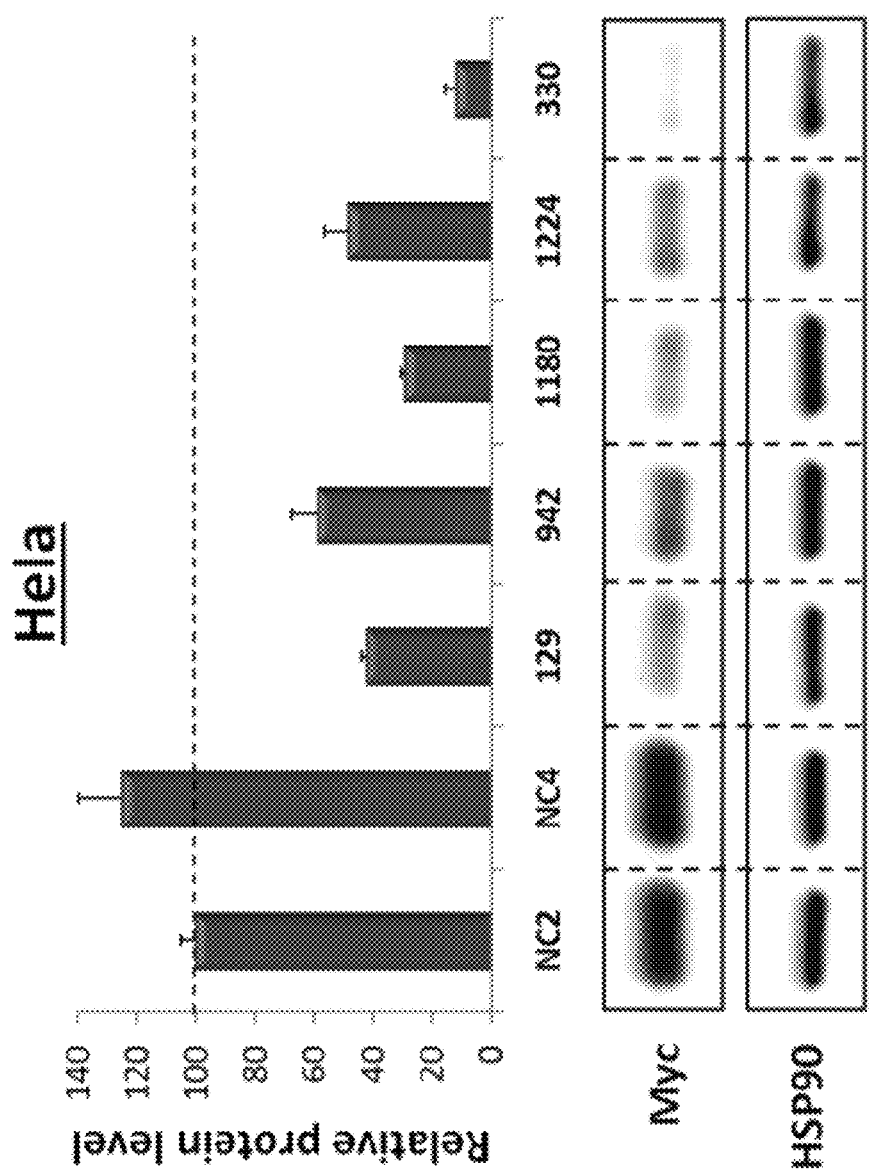
Figure 2A:
FIGS. 2A-2B show that miR-330-5p directly targets MYC MRE-889.
Figure 2B:
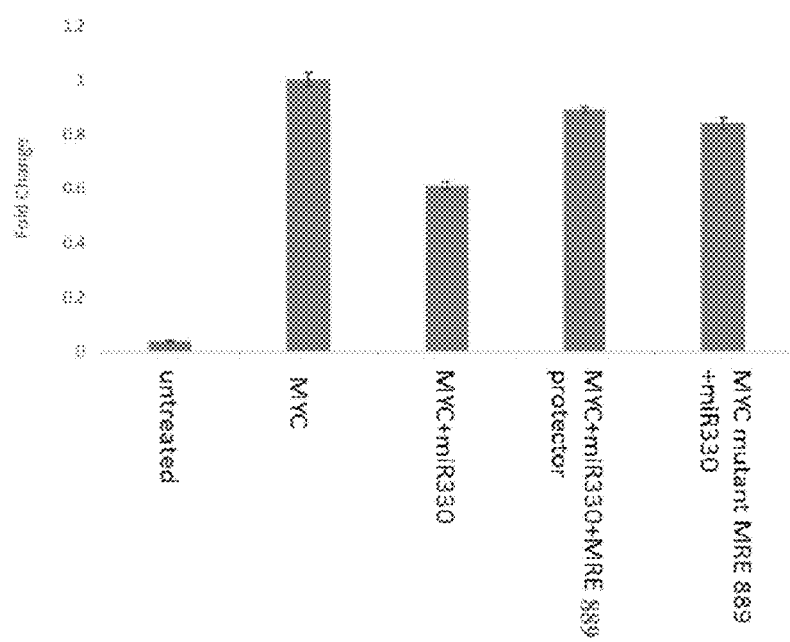
Figure 3A:
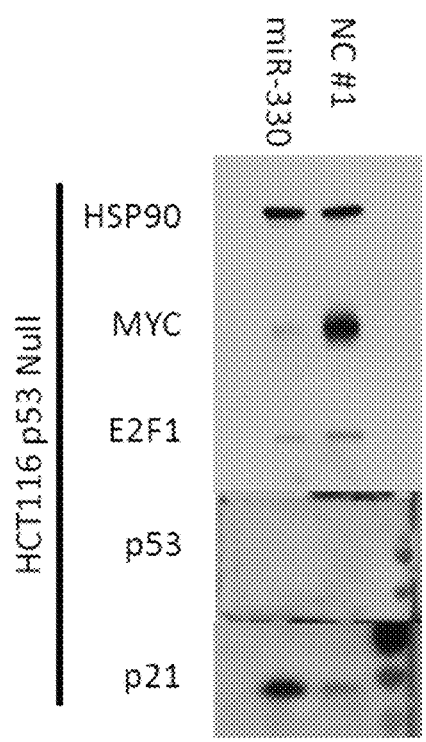
FIGS. 3A-3B show the effects of miR-330 overexpression.
Figure 3B:
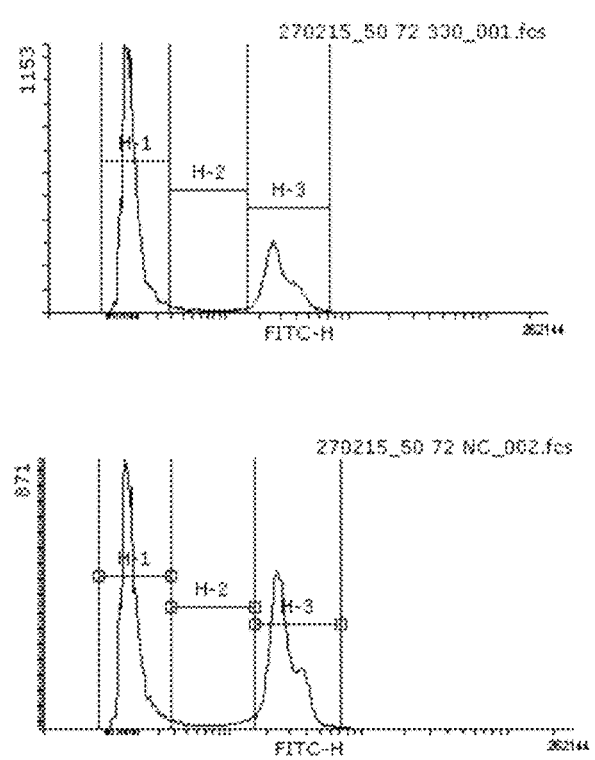
Figure 9A:
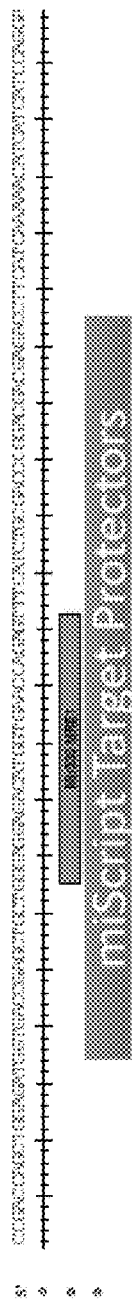
FIGS. 9A-9B depict direct targeting of MYC MRE-889 by hsa-miR-330.
Figure 9B:
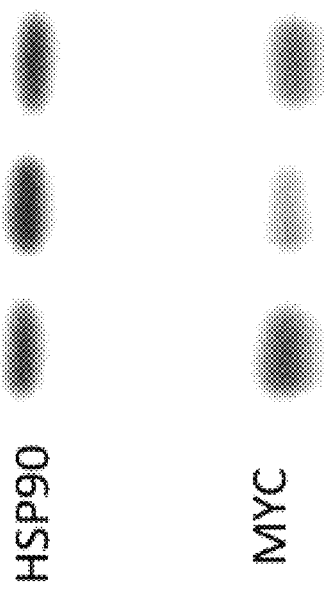
Figure 11:
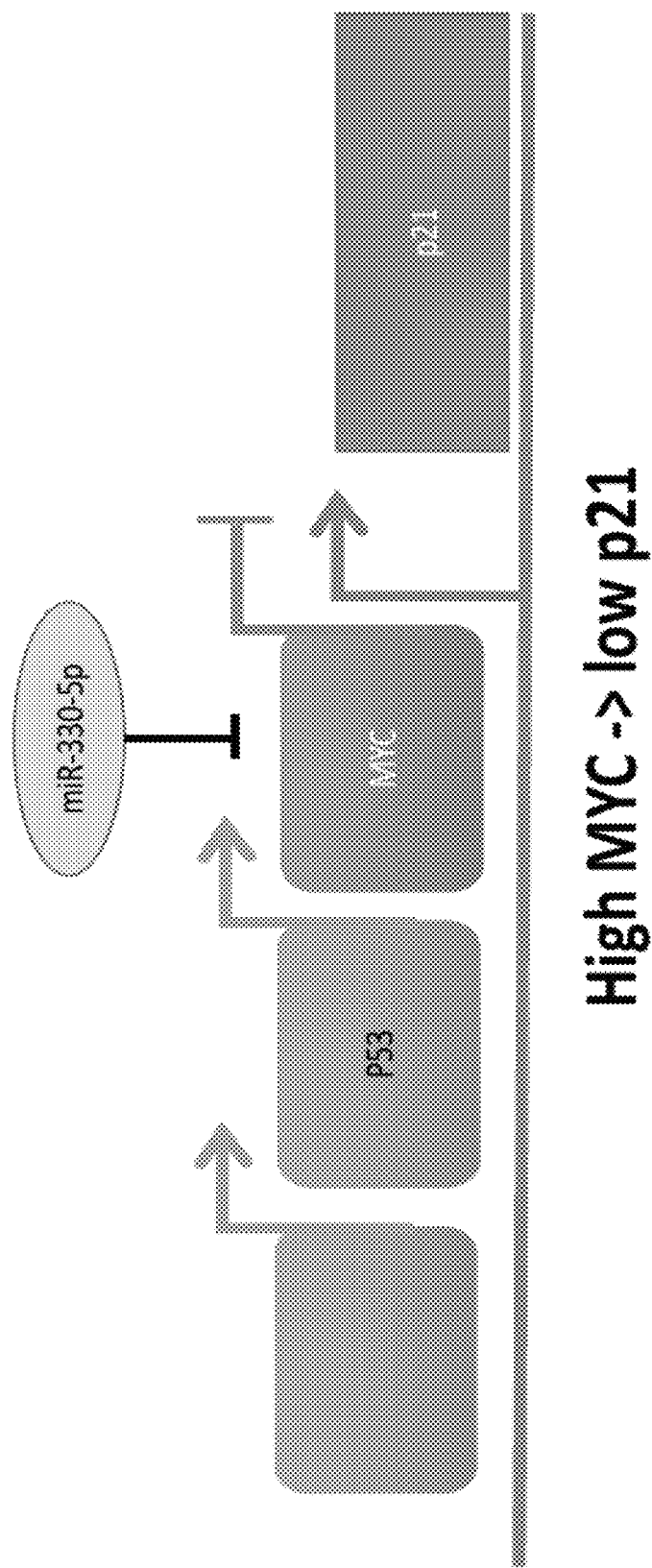
FIG. 11 schematically depicts regulation of p21 by MYC and p53, and shows that high MYC levels result in low levels of p21.
Figures 12A, 12B, 12C:
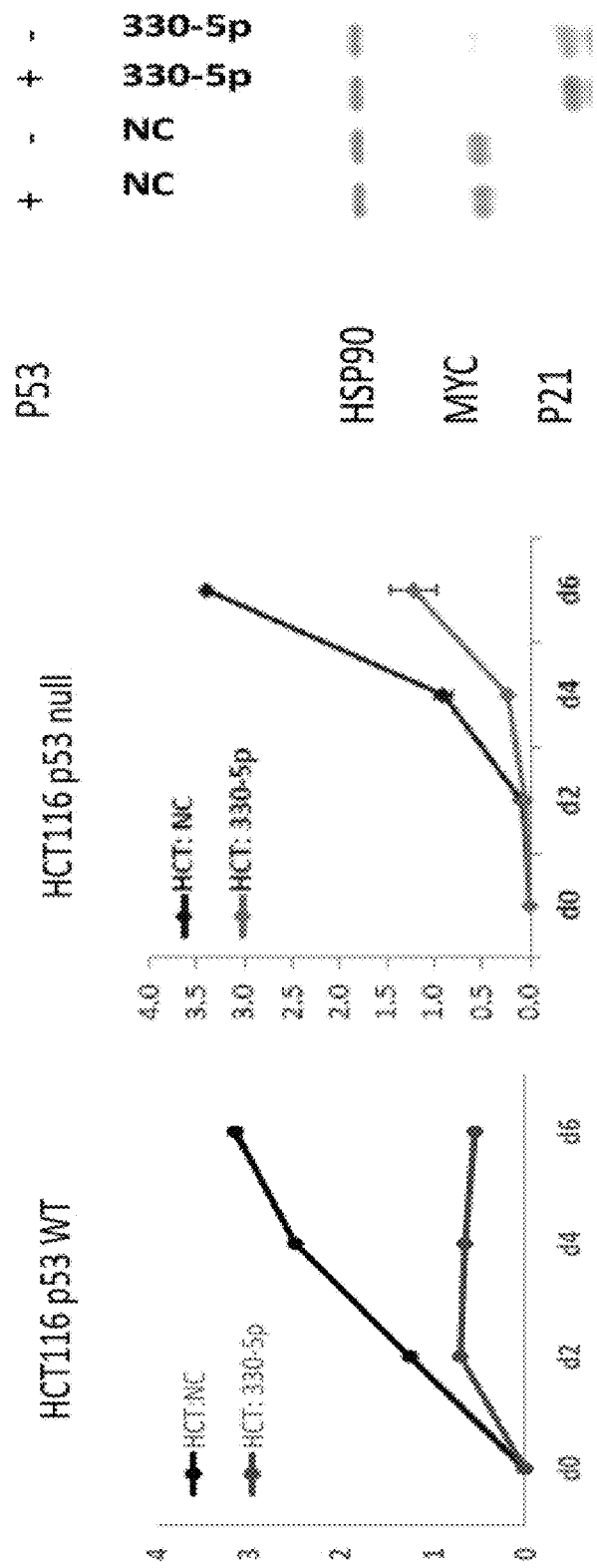
FIGS. 12A-12C depict p21-independent p21 overexpression mediated by hsa-miR-330-5p.
Figures 13A, 13B, 13C:
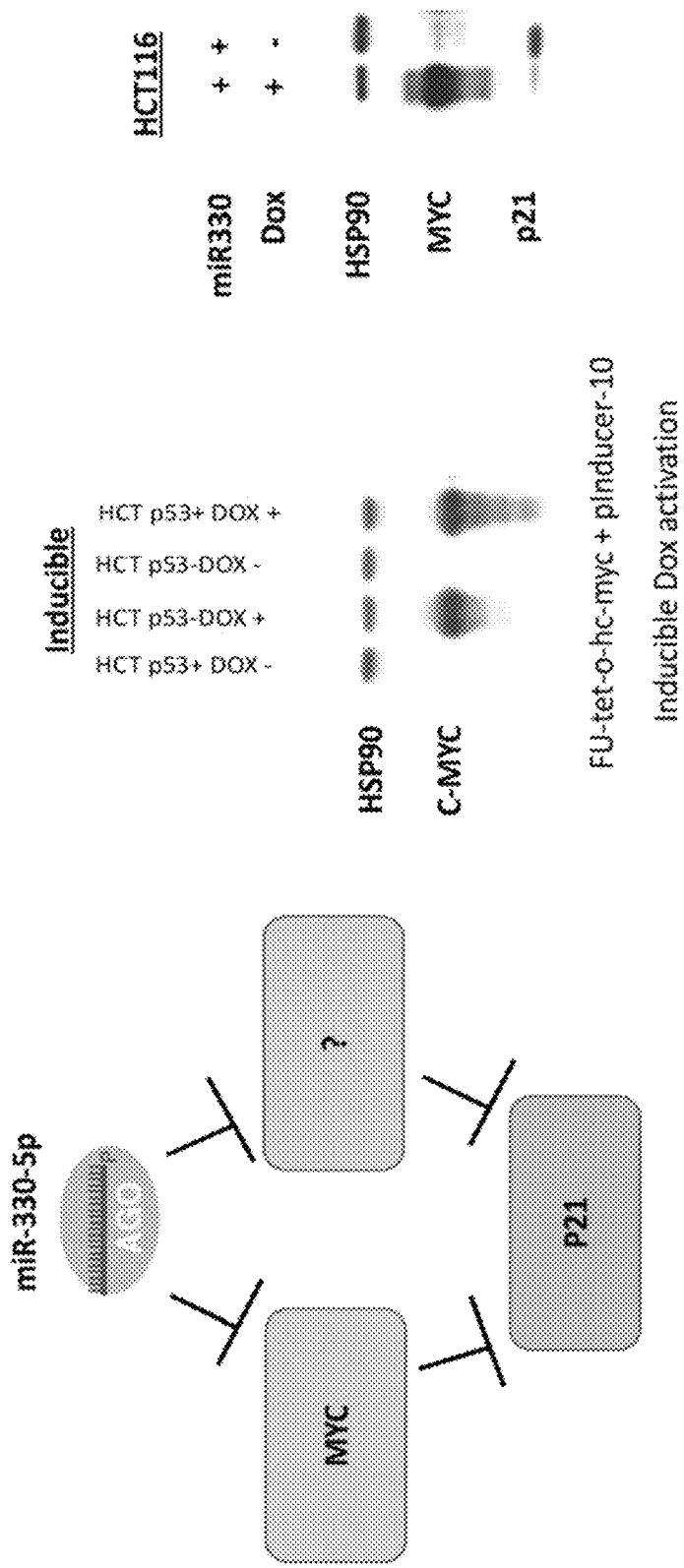
FIGS. 13A-13C depict that MYC overexpression rescues hsa-miR-330-p5 effects.
Figure 14B:
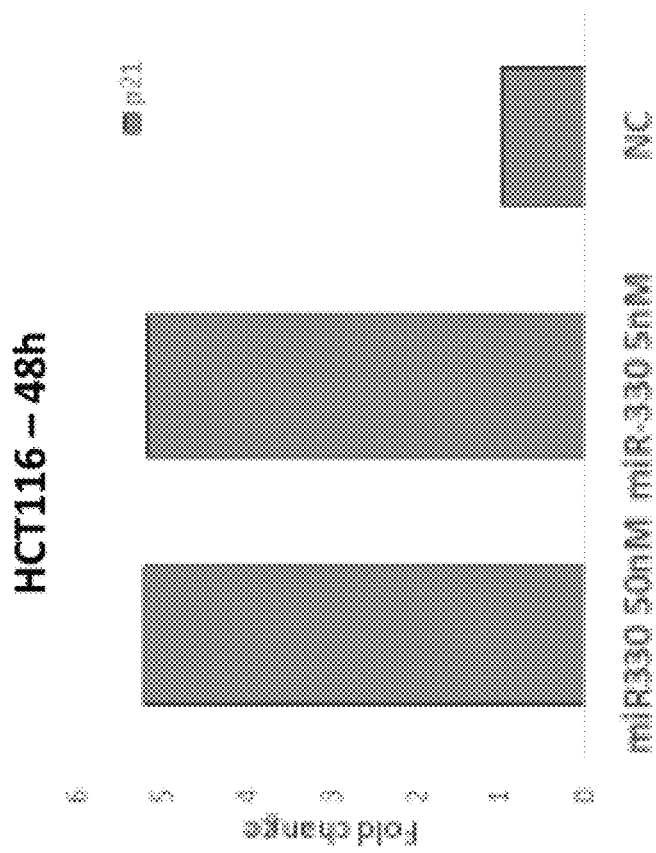
FIGS. 14A-14B depict that low doses of hsa-miR-330-5p induce p21 expression.
Figure 14A:
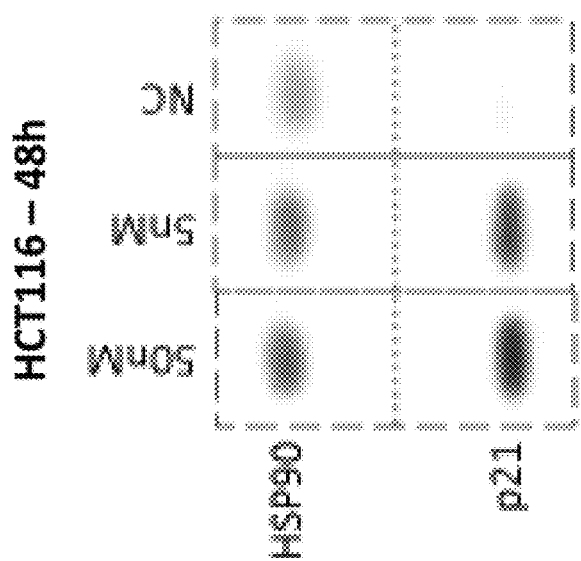
Figures 15A, 15B, 15C:
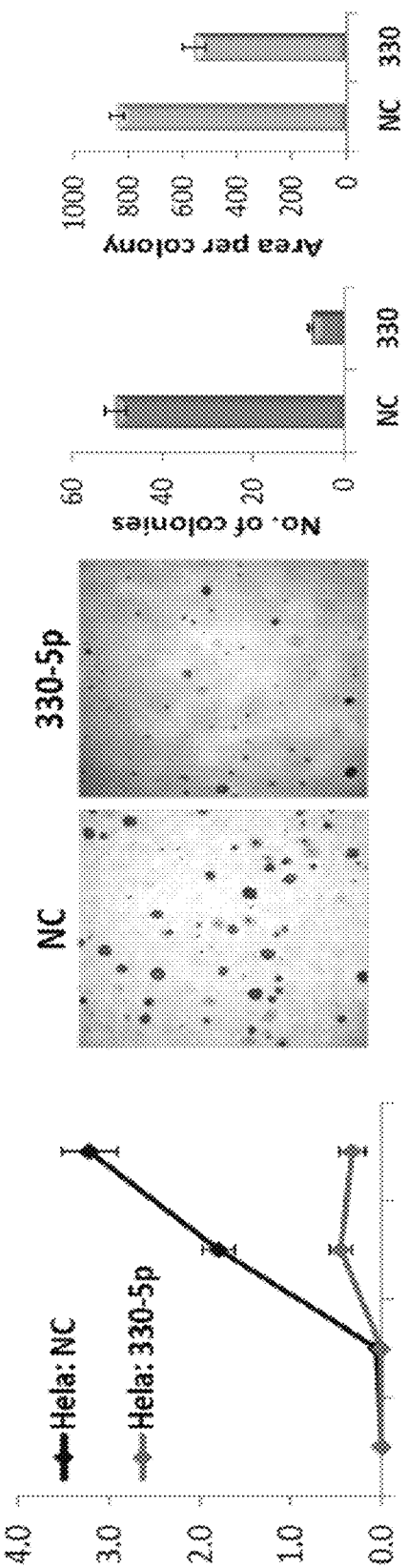
FIGS. 15A-15C depict the characterization of hsa-miR-330-5p as a tumor suppressor.
Figure 16:
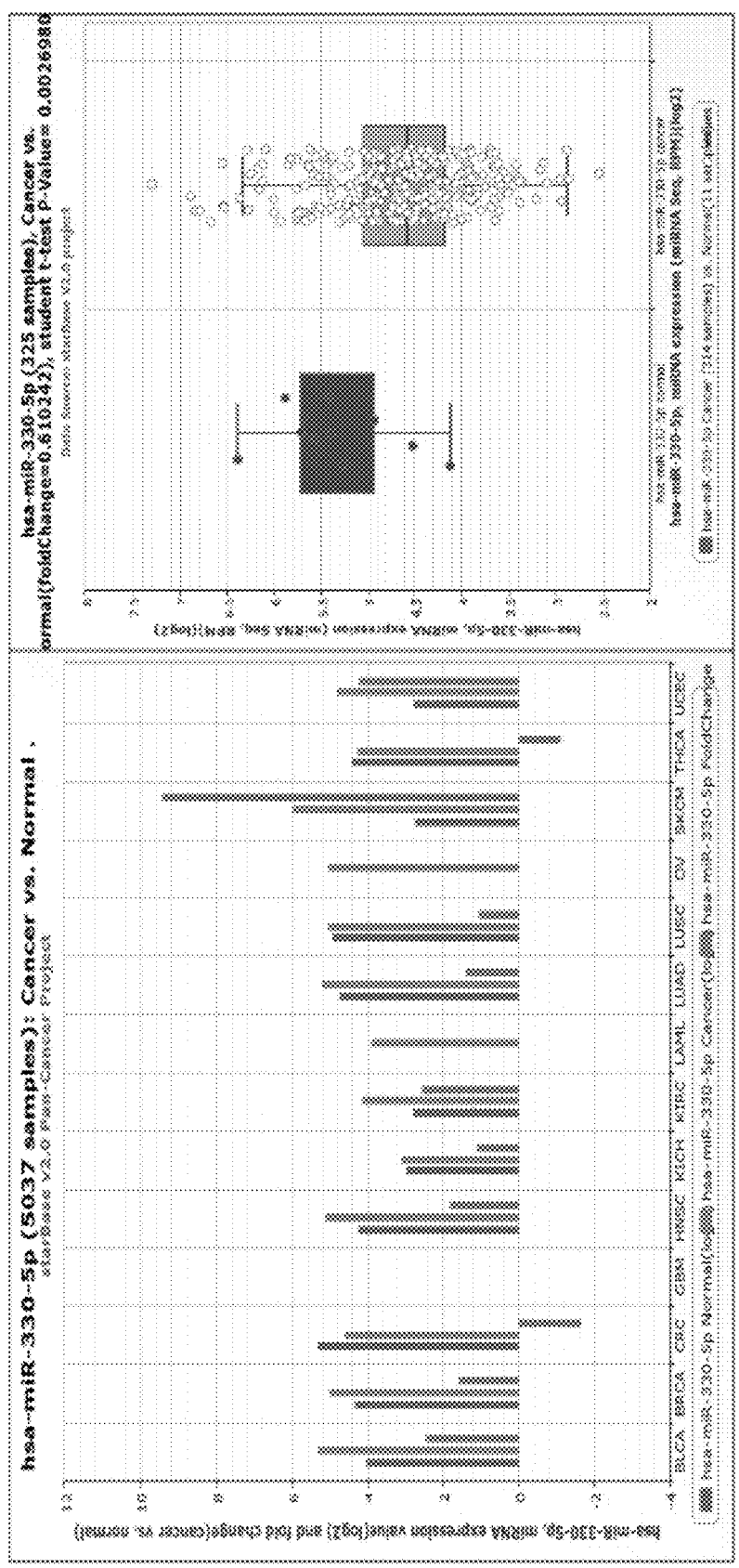
FIG. 16 depicts hsa-miR-330-5p downregulation in colorectal cancer.
Figure 17:
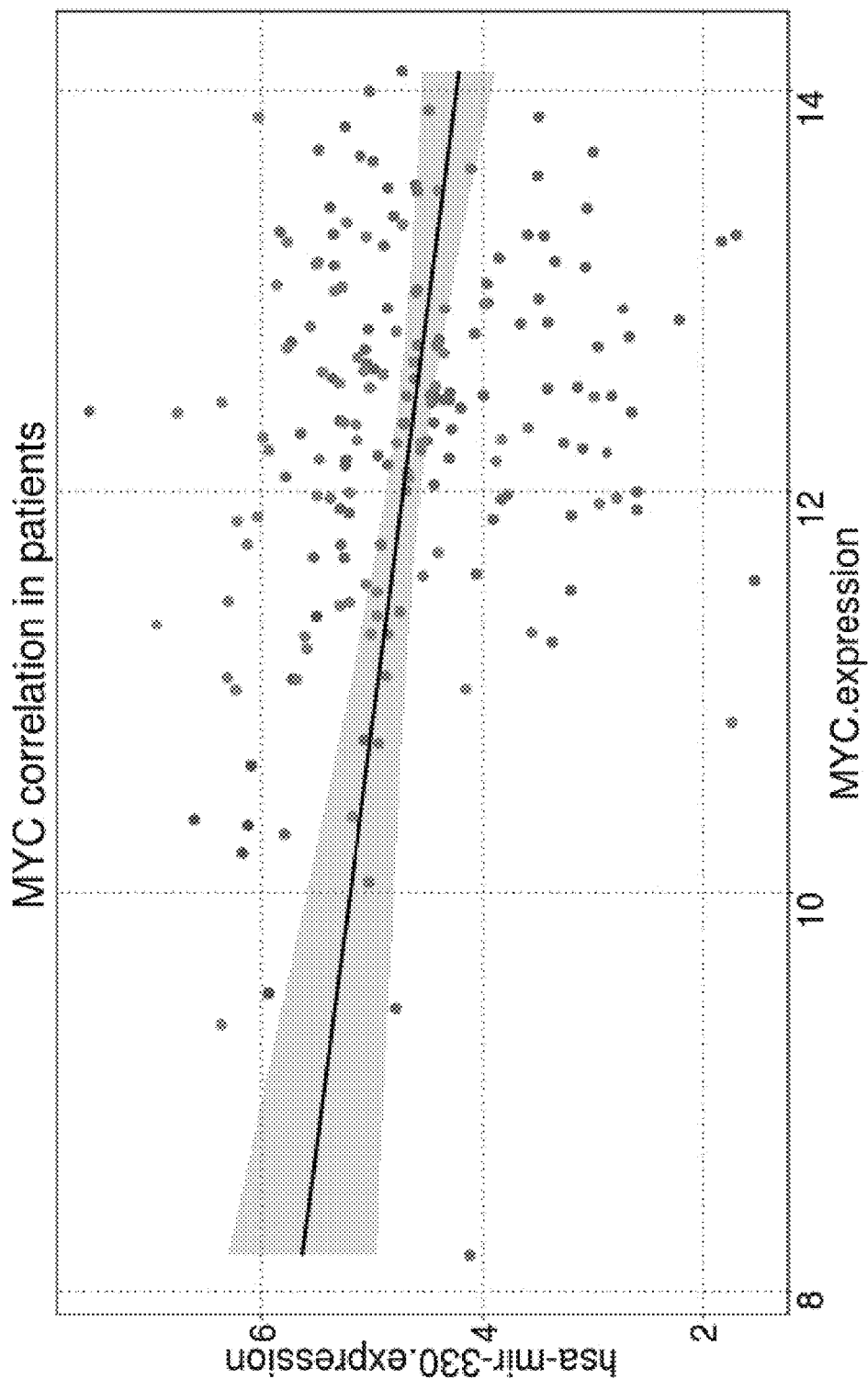
FIG. 17 depicts a negative correlation between MYC and hsa-miR-330-5p in colorectal cancer.
Figure 18:
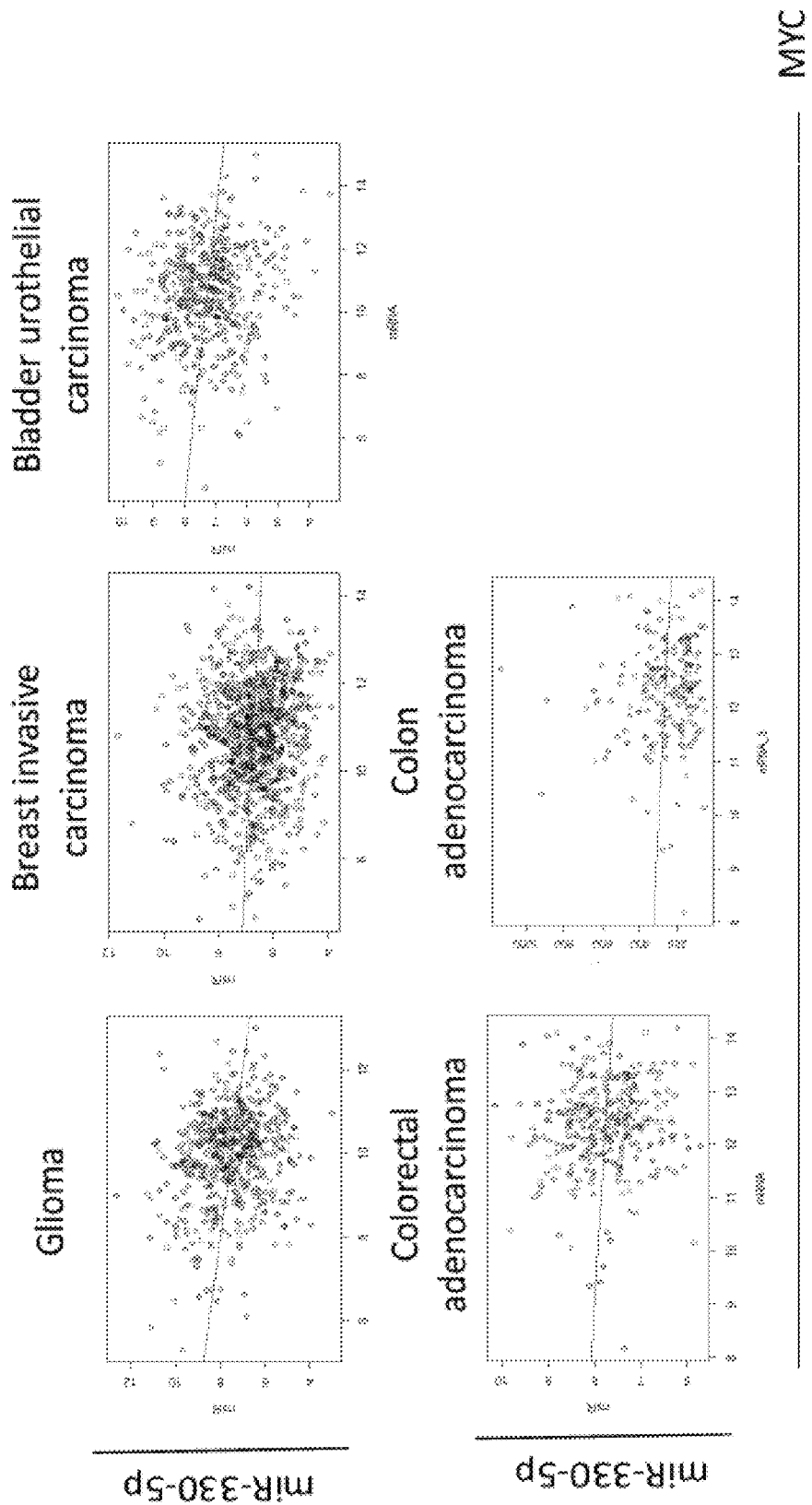
FIG. 18 depicts a negative correlation observed between MYC expression and hsa-miR-330-5p expression in gliomas, breast cancer (invasive carcinoma), bladder urothelial carcinoma, colorectal adenocarcinoma and colon adenocarcinoma.
Figure 19:
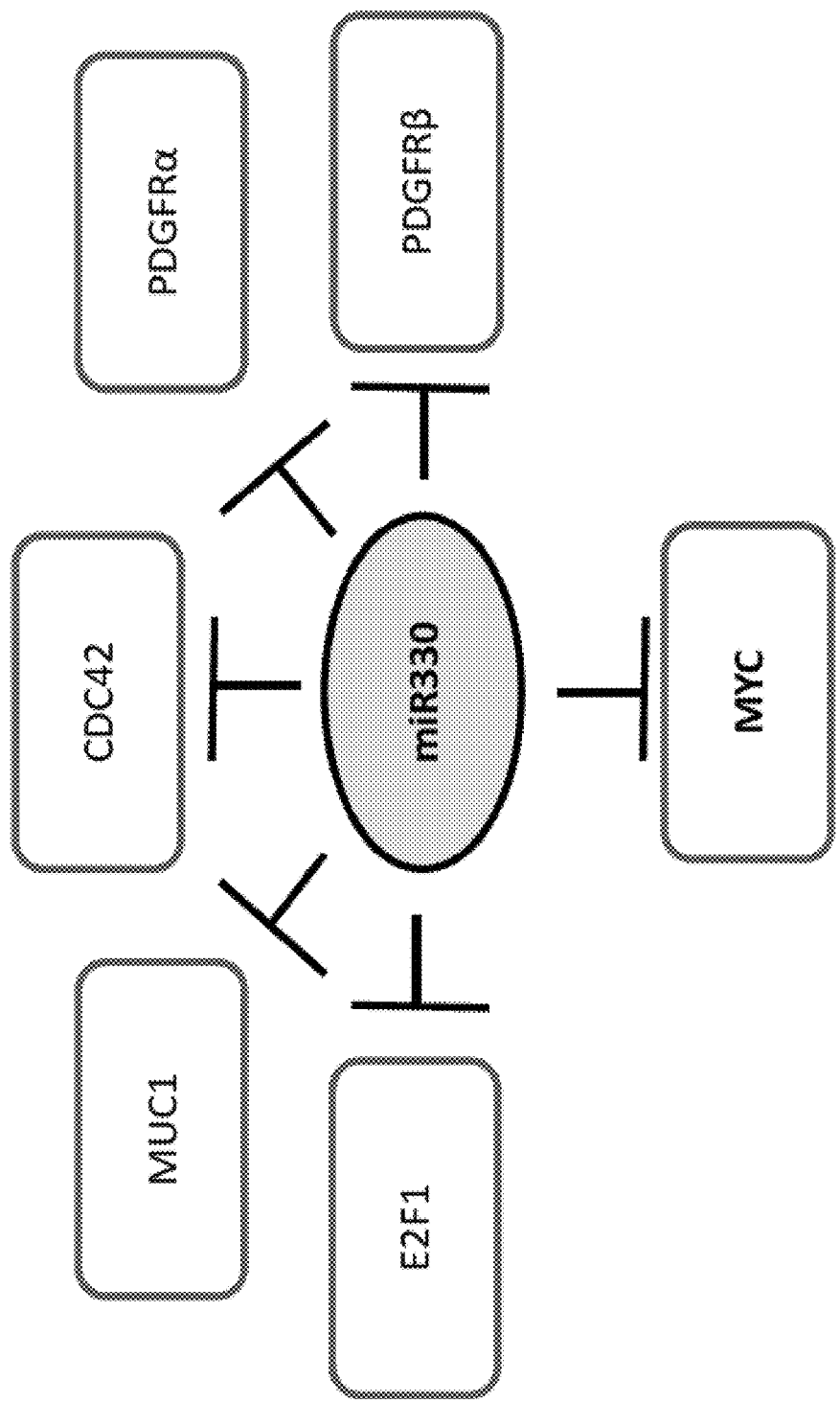
FIG. 19 schematically depicts the tumor-suppressor activity of hsa-miR-330 on several oncogenes.
Figure 20:
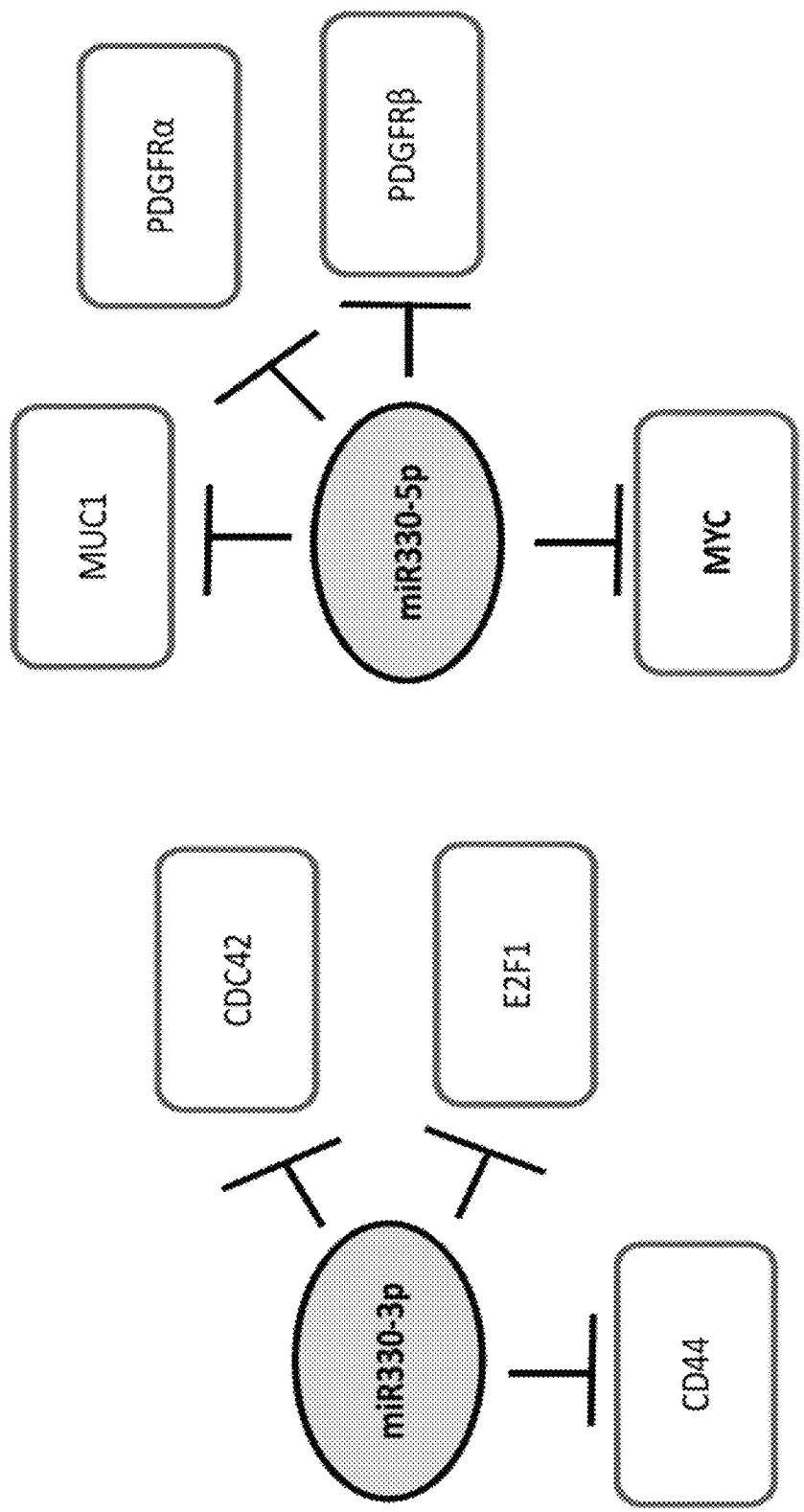
FIG. 20 schematically depicts the tumor-suppressor activity of hsa-miR-330-3p and hsa-miR-330-5p on several oncogenes.

The present invention is based on the identification of a specific miRNA, miR-330, that regulates the expression of MYC, and other oncogenes, such as E2F1, PDGFRa and PDGFRb (FIGS. 1 and 6). Delivery of mimic miR-330-5p to different cancer cells lead to increased levels of the important tumor-suppressor P21, in an p53 independent manner, and strong cell cycle arrest (FIG. 3). In certain embodiments, the present invention provides novel nucleic acid-based compounds, i.e., miR-330 agents, that mimic the function of miR-330 and their use to reduce the proliferating potential of MYC-associated cancer cells (FIGS. 3 and 4).

miR-330 primarily targets MYC in the coding region (FIGS. 1 and 2). While most previous studies have focused on 3'UTR-mediated miRNA regulation. Because the 3'UTRs of many genes tend to be unstable in cancer, the ability to identify miRNAs that target oncogenic coding regions holds great therapeutic potential.

Nucleotide-based therapies are a promising approach in the development of a new generation of anticancer drugs. The present invention describes nucleotide-based mimics of miRNA (e.g., miR-330 agents) that downregulate important oncogenes. For example, the MYC proto-oncogene regulates cell proliferation and fate, and therefore it plays an important role in many types of cancer. Prior to Applicants' discovery, MYC was considered in the field of cancer chemotherapy to be undruggable.

Novel nucleotide-based mimics of miRNA described herein are capable of targeting MYC and other oncogenes to treat MYC-associated cancers. In combination with diverse delivery systems, the compounds described herein are capable of mimicking an endogenous microRNA that targets a specific type of cancer cell to prevent its proliferation, survival and stemness, i.e., the ability to self-renew and differentiate into different tumor cell types. Such compounds can work as a combination of different mimic microRNAs and microRNAs inhibitors to create a unique combination therapy based on the specific genetics of a given patient.

Example II

MYC and miR-330—A Role in Hepatocellular Carcinoma

Figures 21A, 21B, 21C:
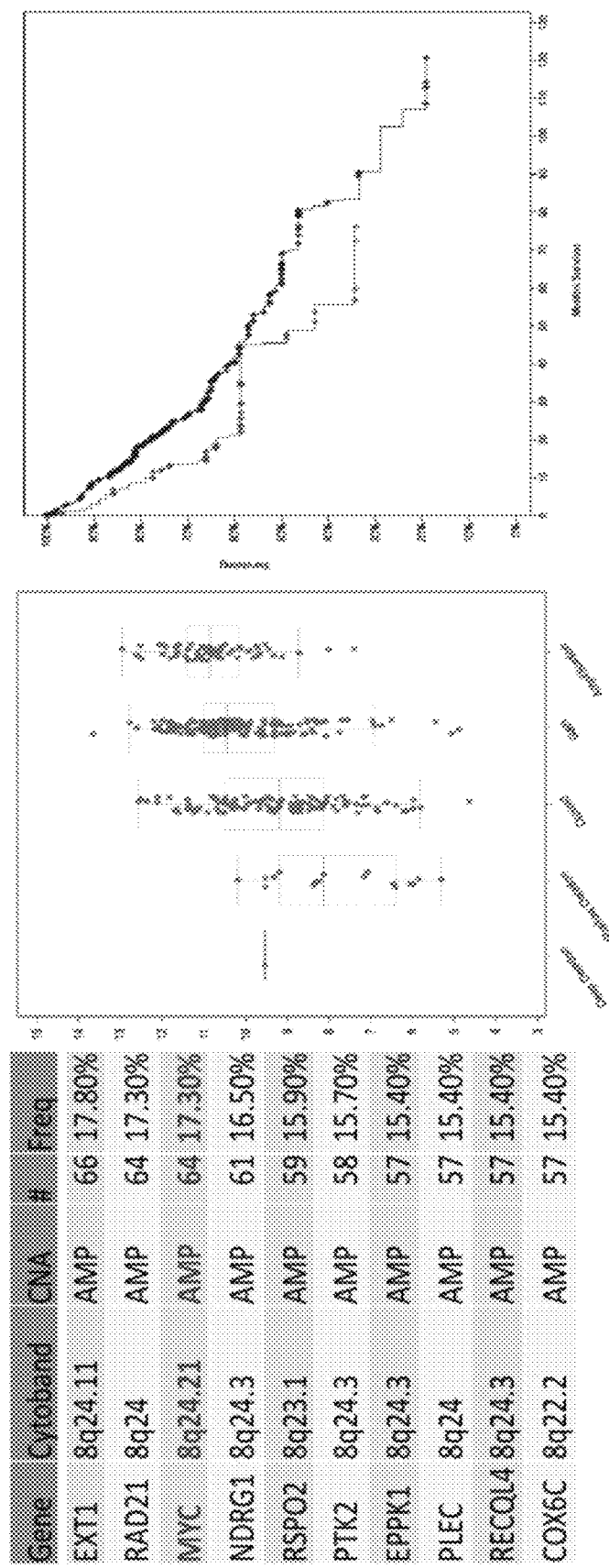
FIGS. 21A-21C depicts MYC amplification and overexpression in hepatocellular carcinoma (HCC).
Figure 22:
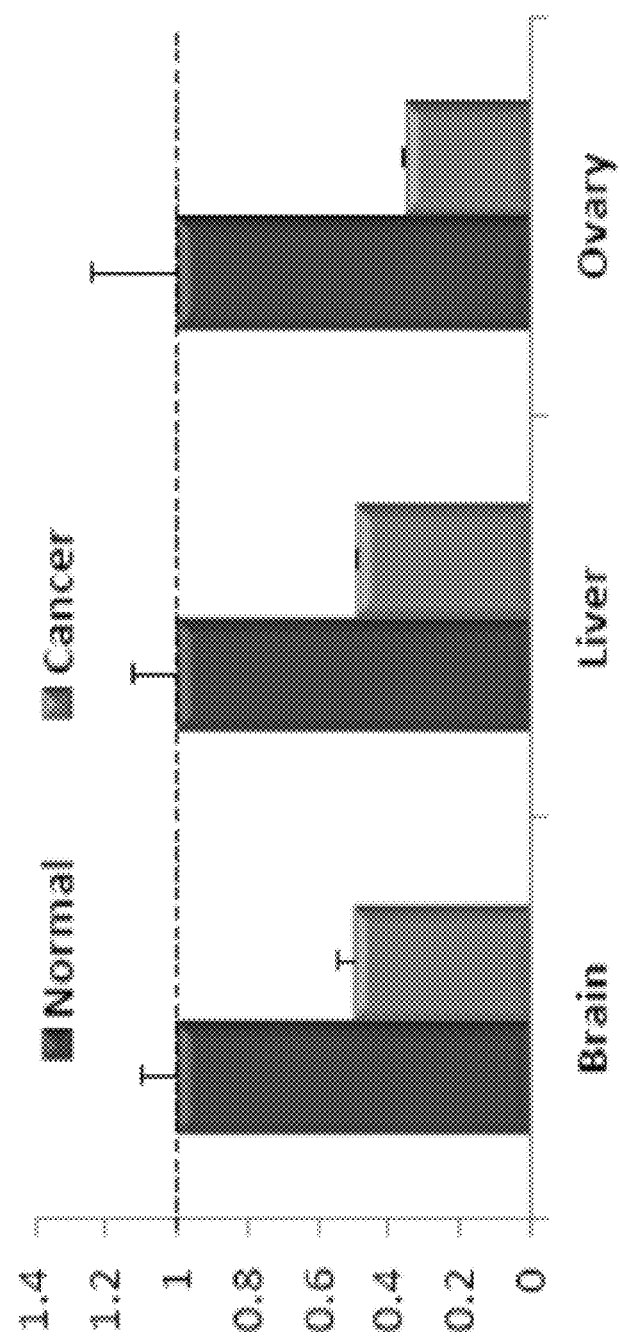
FIG. 22 depicts a decrease in hsa-miR-330-5 levels in liver cancer.
Figure 23:
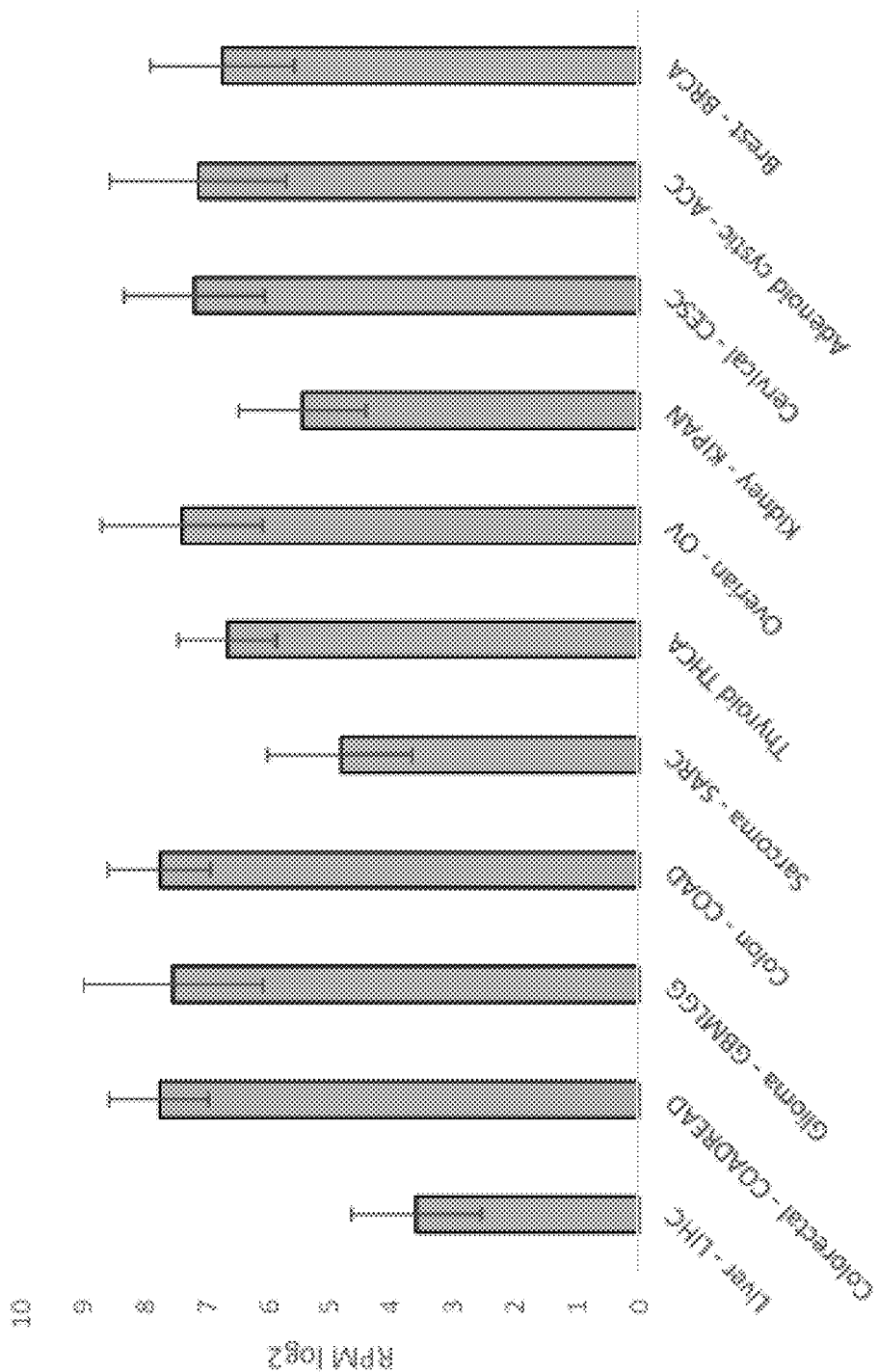
FIG. 23 depicts a relative decrease in hsa-miR-330-5 levels in liver cancer when compared with hsa-miR-330-5 levels in a variety of other cancers.

MYC was determined to be amplified and overexpressed in human hepatocellular carcinoma (HCC) cells, and correlated with poor survival (FIG. 21). miR-330-5p levels were determined to be decreased in liver cancer (FIGS. 22 and 23).

miR-330 function was studied in HCC cell lines as well as in mouse models.

In vitro study of miR-330 in HCC cell lines was performed in cells from Hep 3B mice (male, hepatitis B positive, p53 null, forms tumors in nude mice) and Hep G2 mice (male, hepatitis B negative, p53 WT, forms colonies in semi-solid medium). In vitro analysis of miR-330 expression was performed. miR-330 overexpression was determined to reduce MYC levels, cell proliferation, cell cycle, apoptosis, migration and growth in soft agar. miR-330 inhibition was determined to increase MYC levels, cell proliferation and tumorigenicity.

Figure 24:
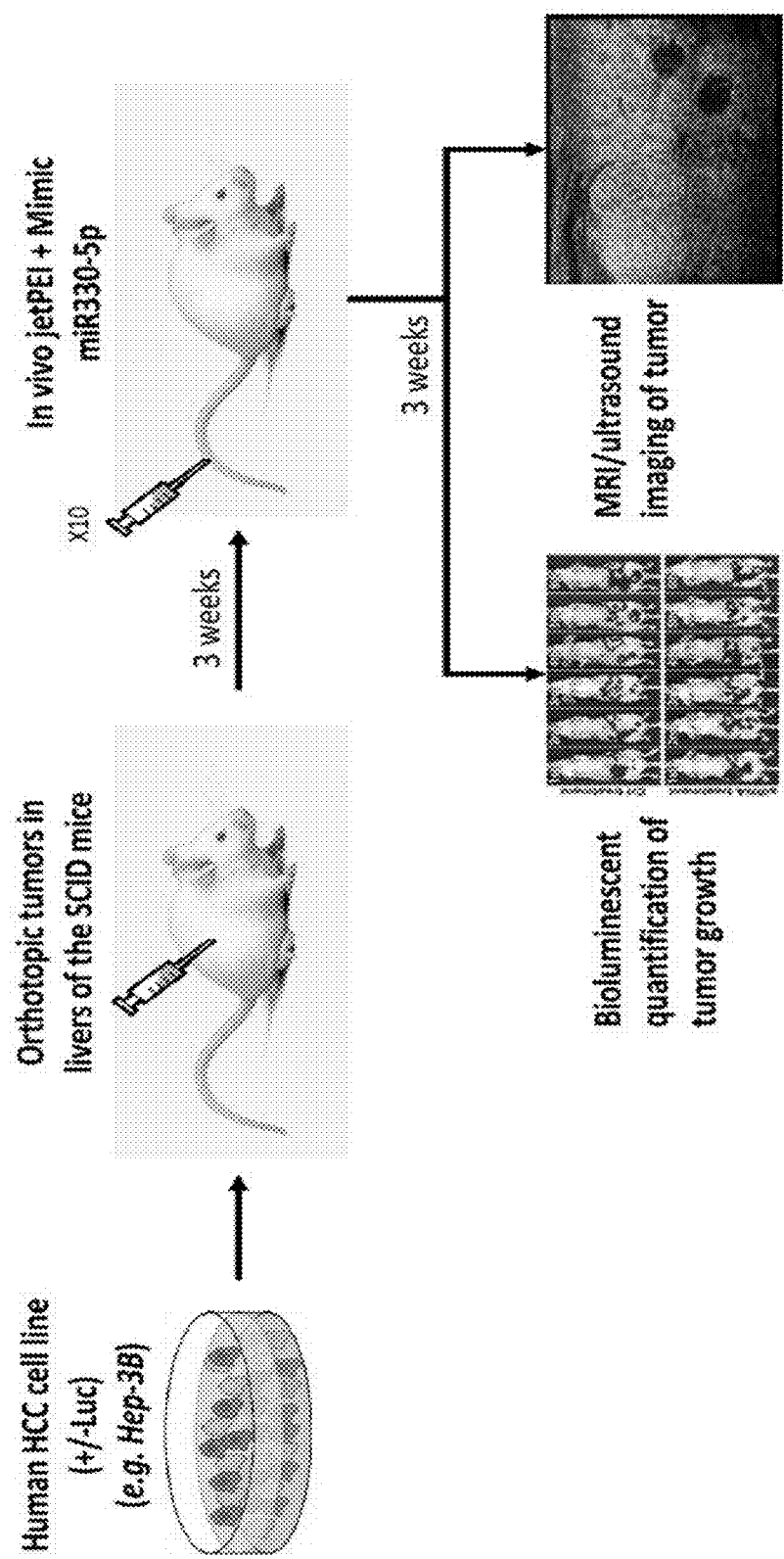
FIG. 24 schematically depicts in vivo targeting of human HCC with miR-330 mimics according to certain aspects of the invention.

In vivo delivery of miR-330 was studied in mouse models. Intra-tumor delivery to xenograft tumors was performed using jetPEI (Polyplus) and miRIDAN (from Dharmacon, Inc., Lafayette, Colo.). Systemic delivery to orthotopic tumors was also performed using jetPEI (Polyplus) and miRIDAN. (See FIGS. 24 and 25.)

Figure 26B:
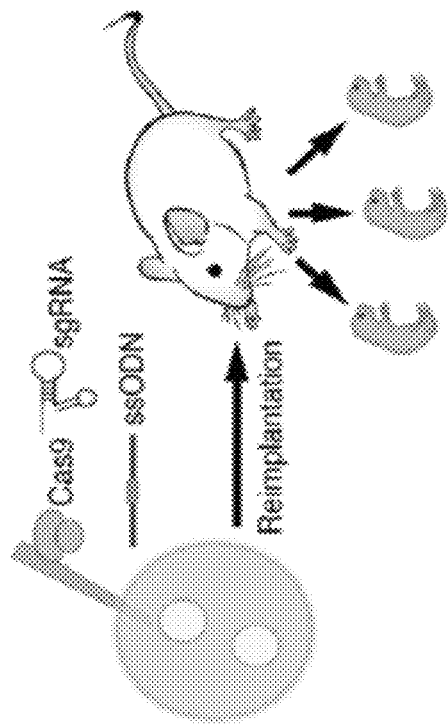
FIGS. 26A-26B depict a CRISPR/Cas9-based approach to analyze miR-330 in vivo.
Figure 26A:
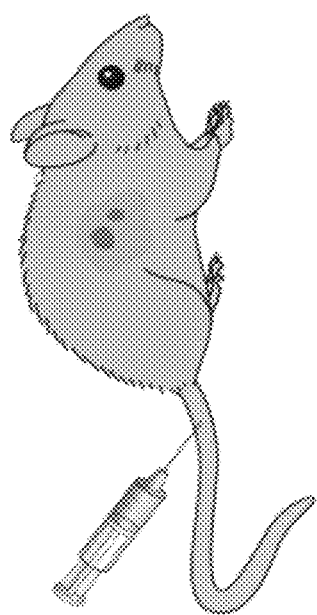
Figure 27:
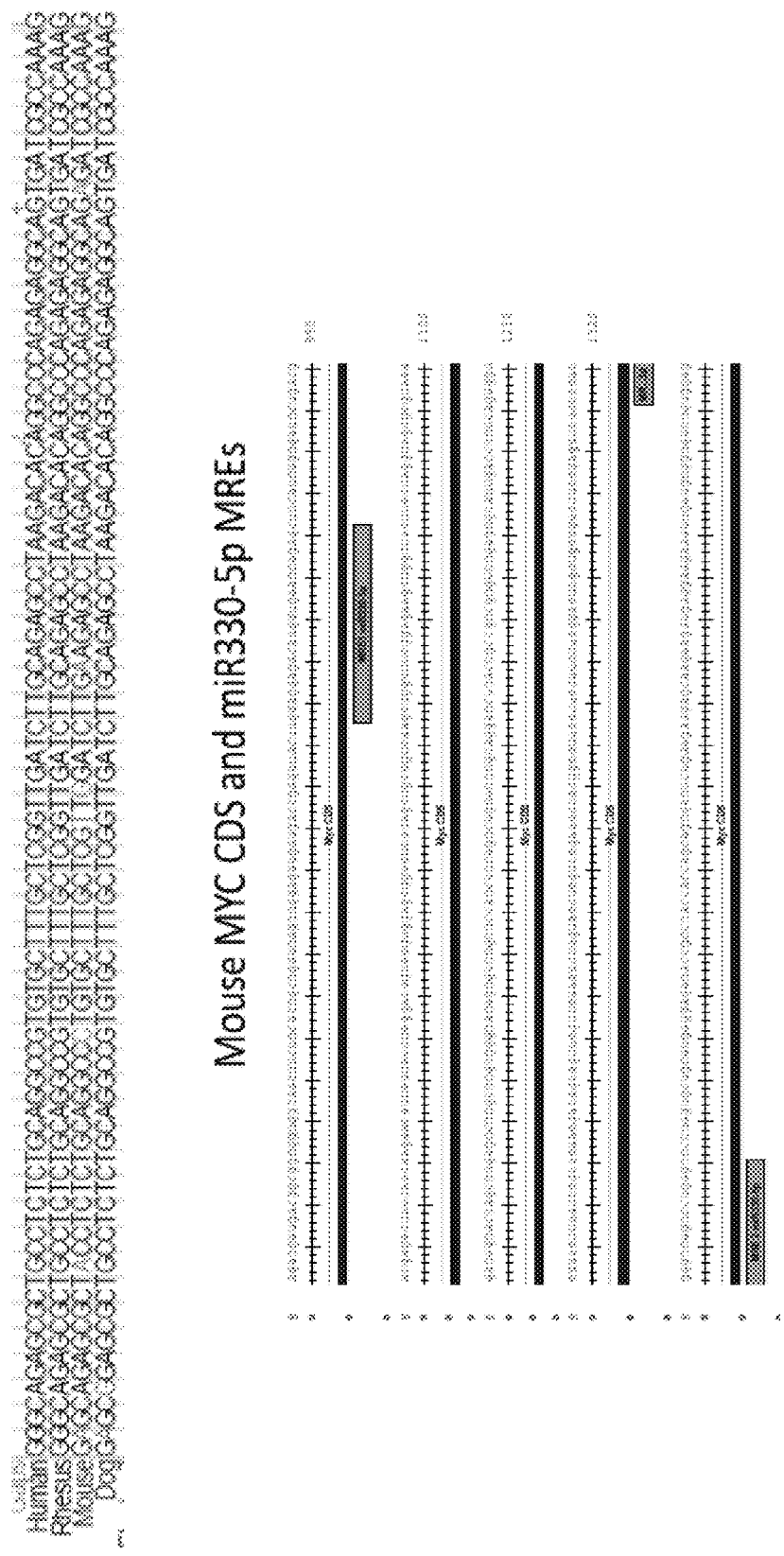
FIG. 27 depicts the conservation of mouse miR-330-5p and mouse MYC MRE1 and MRE2 as compared to human. Figure discloses SEQ ID NOS 37-40 and 44, respectively, in order of appearance.
Figure 28:
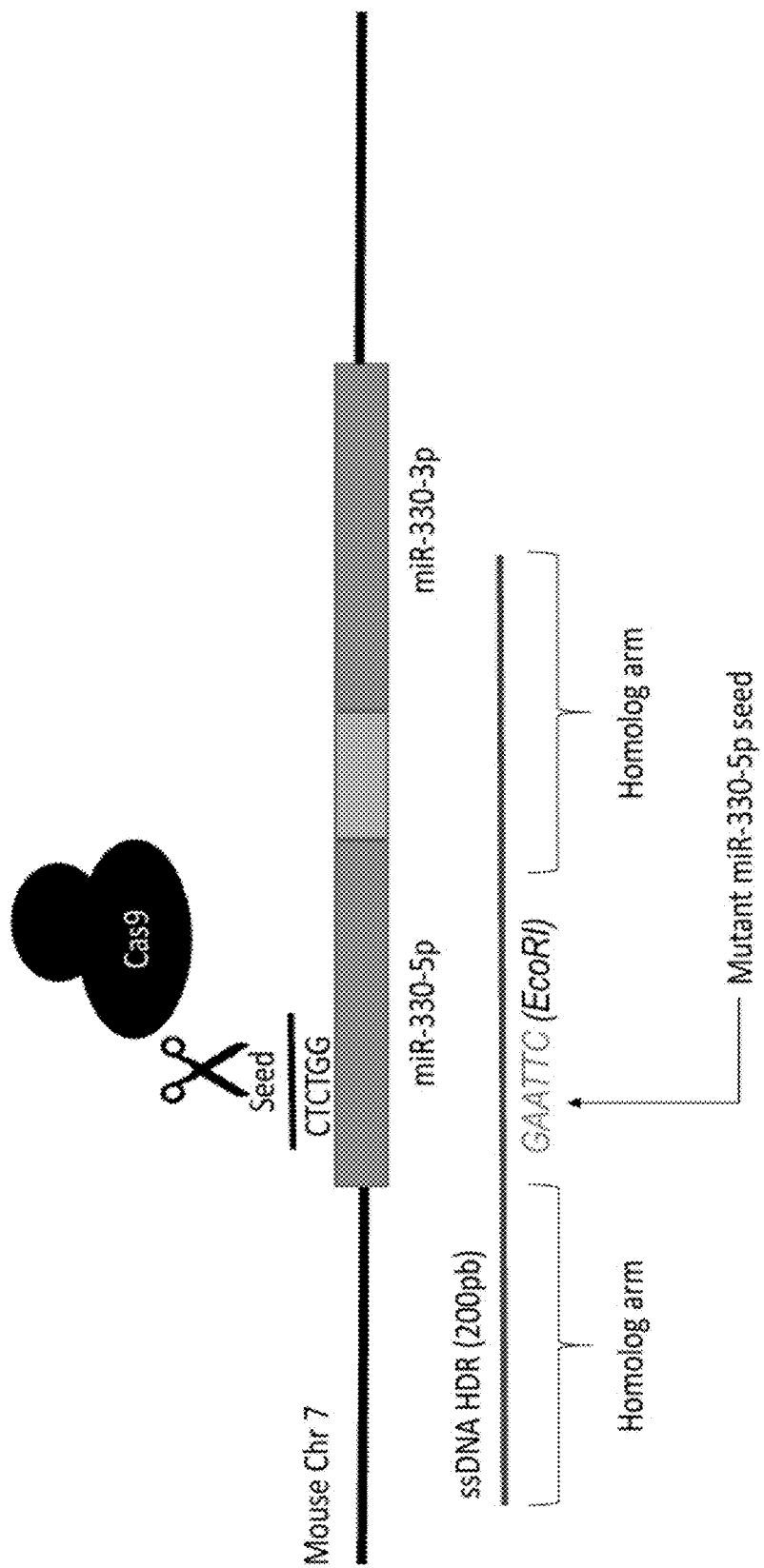
FIG. 28 schematically depicts CRISPR/Cas9 mutation of miR-330-5p in a mouse model.
Figures 29A, 29B, 29C:
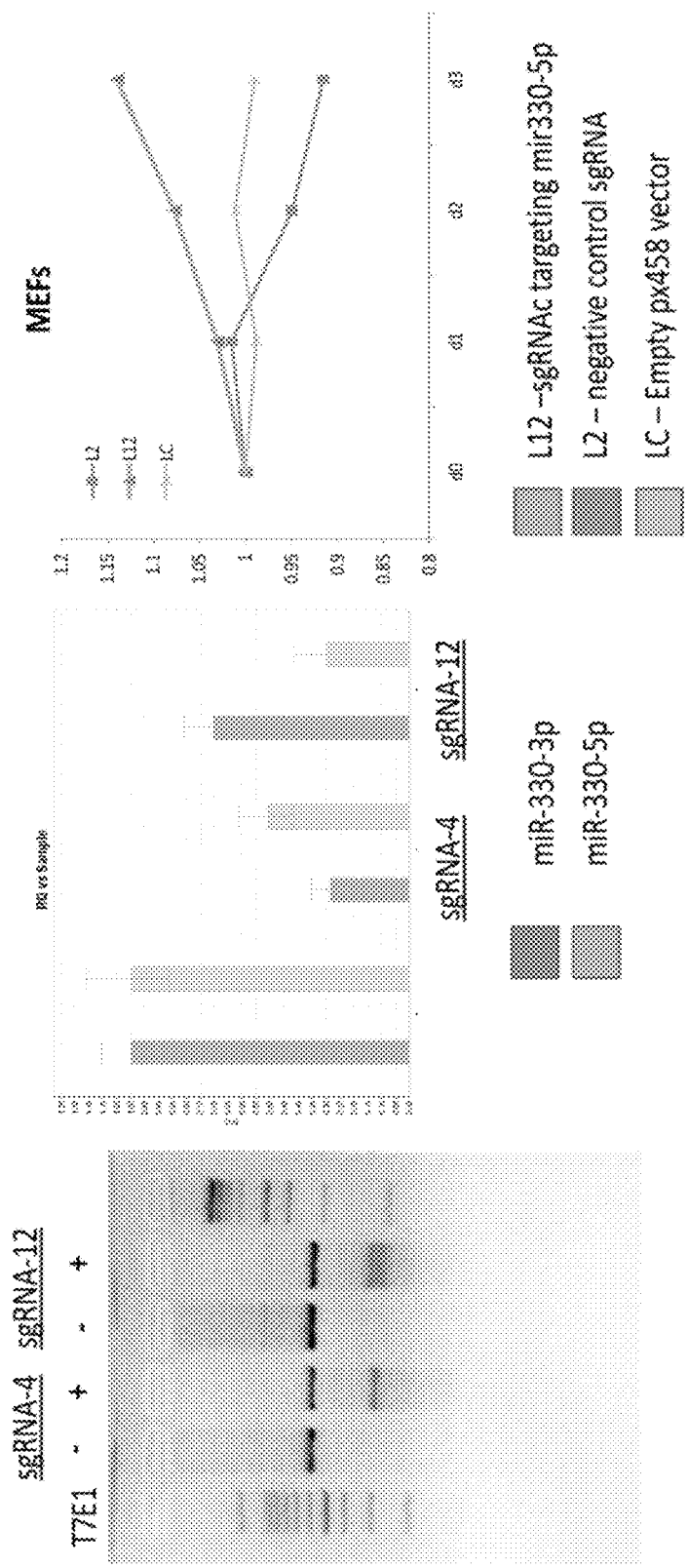
FIGS. 29A-29C depict mouse miR-330 CRISPR-Cas9 knockout in immortalized 3T3 MEFs.

A CRISPR/Cas-9-based protocol was also used to analyze miR-330 activity in vivo (FIGS. 26-28). Mice were obtained that had decreased miR-330-5p and miR-330-3p after CRISPR/Cas-9 knockout of miR-330 (FIG. 29).

Thus, it was determined that miR-330 is a suppressor of MYC and other oncogenes. It was further determined that miR-330 is downregulated in HCC cells.

In exemplary embodiments, the following therapeutic potential using the miR-330 agents described herein are provided based on the results described herein:
1. miR-330 delivery to the liver targeting MYC-dependent HCC cells;
2. miR-330 delivery in combination with other miRNAs (e.g., other MYC-targeting miRNAs)/RNAi for multi targets effects; and
3. miR-330 delivery in combination with other drugs/therapeutics protocols for personalized medicine.

Example III miR-330-5p as Cancer Therapy

As a unique therapy approach, modified miR330-5p is expressed in cancer cells. To deliver and overexpress miR-330-5p in a non-viral approach, a double-stranded 2'-O-methyl (2'-O-Me) modified ribonucleotide is generated based on the endogenous human miR330-5p, with phosphoromonothioate modifications. DNA modifications are introduced to the 3' overhangs to increase stability and efficiency.

In addition, a viral-based approach is used for delivery and overexpression of mir330. The sequences of mature miR330-5p and 3p are cloned with a mir30 loop. The modified mir330 sequence is cloned into a lentiviral-based vector or an adeno associated virus (AAV)-based vector, which have the ability to efficiently infect human cells in vivo.

What is claimed:

1. A method of treating a MYC-associated cancer in a subject in need thereof, the method comprising:
    selecting a subject that overexpresses MYC; and
    administering to the subject a pharmaceutical composition comprising a nucleic acid sequence having at least 80% complementarity to a micro RNA (miR) Responsive Element (MRE) sequence set forth as SEQ ID NO:1, thereby treating cancer in the subject, wherein the MYC-associated cancer is further characterized by downregulation of hsa-miR-330-5p.

2. The method of claim 1, wherein the nucleic acid sequence has at least 90% complementarity, 95% complementarity, or 98% complementarity to the MRE sequence set forth as SEQ ID NO:1.

3. The method of claim 1, wherein the nucleic acid sequence is further perfectly complementary to an MRE seed sequence set forth as SEQ ID NO:2.

4. The method of claim 1, wherein the nucleic acid sequence comprises a miRNA or an siRNA, optionally wherein the miRNA is a miR-330-5p compound.

5. The method of claim 4, wherein the miRNA or siRNA is between 20 and 24 nucleotides in length.

6. The method of claim 1, wherein the MRE is a MYC MRE.

7. The method of claim 1, wherein MYC expression is downregulated in the subject after administering the pharmaceutical composition to the subject.

8. The method of claim 1, wherein MYC mRNA cleavage is mediated or translation of MYC mRNA is inhibited.

9. The method of claim 1, wherein the MYC-associated cancer is liver cancer or colorectal cancer.

10. The method of claim 1, wherein the nucleic acid sequence is administered using a recombinant Adeno-Associated virus (AAV).

11. The method of claim 1, wherein the nucleic acid sequence is a double-stranded nucleic acid sequence having a sense strand and an antisense strand, wherein the antisense strand has at least 80% complementarity to the MRE sequence.

12. A method of targeting MYC overexpression in a cancer cell characterized by overexpression of MYC, comprising contacting the cell with a nucleic acid sequence having at least 80% complementarity to an MRE sequence set forth as SEQ ID NO:1 to inhibit translation of the MYC mRNA, wherein the cancer cell is further characterized by downregulation of hsa-miR-330-5p.

13. The method of claim 12, wherein the nucleic acid sequence comprises a miRNA or an siRNA, optionally wherein the miRNA is a miR-330-5p compound.

* * * * *

SEQUENCE LISTING

```
<160> NUMBER OF SEQ ID NOS: 44

<210> SEQ ID NO 1
<211> LENGTH: 22
<212> TYPE: DNA
<213> ORGANISM: Homo sapiens

<400> SEQUENCE: 1
aggagacatg gtgaaccaga gt                                              22

<210> SEQ ID NO 2
<211> LENGTH: 6
<212> TYPE: DNA
<213> ORGANISM: Homo sapiens

<400> SEQUENCE: 2 ccagag                                                                 6

<210> SEQ ID NO 3
<211> LENGTH: 22
<212> TYPE: RNA
<213> ORGANISM: Homo sapiens

<400> SEQUENCE: 3
ucucugggcc ugugucuuag gc                                              22

<210> SEQ ID NO 4
<211> LENGTH: 94
<212> TYPE: RNA
```

<213> ORGANISM: Homo sapiens

<400> SEQUENCE: 4
cuuuggcgau cacugccucu cugggccugu gucuuaggcu cugcaagauc aaccgagcaa    60
agcacacggc cugcagagag gcagcgcucu gccc    94

<210> SEQ ID NO 5
<211> LENGTH: 23
<212> TYPE: RNA
<213> ORGANISM: Homo sapiens

<400> SEQUENCE: 5
gcaaagcaca cggccugcag aga    23

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucucugggcc ugugucuuag gc    22

<210> SEQ ID NO 7
<211> LENGTH: 21
<212> TYPE: DNA
<213> ORGANISM: Homo sapiens

<400> SEQUENCE: 7
tgaccgagct gctgggagga g    21

<210> SEQ ID NO 8
<211> LENGTH: 21
<212> TYPE: DNA
<213> ORGANISM: Homo sapiens

<400> SEQUENCE: 8
gccaagctcg tctcagagaa g    21

<210> SEQ ID NO 9
<211> LENGTH: 21
<212> TYPE: DNA
<213> ORGANISM: Homo sapiens

<400> SEQUENCE: 9
aggcaggctc ctggcaaaag g    21

<210> SEQ ID NO 10
<211> LENGTH: 21
<212> TYPE: DNA
<213> ORGANISM: Homo sapiens

<400> SEQUENCE: 10
agcccactgg tcctcaagag g    21

<210> SEQ ID NO 11
<211> LENGTH: 21
<212> TYPE: DNA
<213> ORGANISM: Homo sapiens

<400> SEQUENCE: 11

```
aggtcctcgg acaccgagga g                                           21

<210> SEQ ID NO 12
<211> LENGTH: 22
<212> TYPE: DNA
<213> ORGANISM: Homo sapiens

<400> SEQUENCE: 12
gccgccaagc tcgtctcaga ga                                          22

<210> SEQ ID NO 13
<211> LENGTH: 22
<212> TYPE: DNA
<213> ORGANISM: Homo sapiens

<400> SEQUENCE: 13
caacgtcttg gagcgccaga gg                                          22

<210> SEQ ID NO 14
<211> LENGTH: 22
<212> TYPE: DNA
<213> ORGANISM: Homo sapiens

<400> SEQUENCE: 14
cctgcgtgac cagatcccgg ag                                          22

<210> SEQ ID NO 15
<211> LENGTH: 22
<212> TYPE: DNA
<213> ORGANISM: Homo sapiens

<400> SEQUENCE: 15
ggtgaccgag ctgctgggag ga                                          22

<210> SEQ ID NO 16
<211> LENGTH: 22
<212> TYPE: DNA
<213> ORGANISM: Homo sapiens

<400> SEQUENCE: 16
gccaagctcg tctcagagaa gc                                          22

<210> SEQ ID NO 17
<211> LENGTH: 22
<212> TYPE: DNA
<213> ORGANISM: Homo sapiens

<400> SEQUENCE: 17
actctgagga ggaacaagaa ga                                          22

<210> SEQ ID NO 18
<211> LENGTH: 22
<212> TYPE: DNA
<213> ORGANISM: Homo sapiens

<400> SEQUENCE: 18
aggtcctcgg acaccgagga ga                                          22

<210> SEQ ID NO 19
<211> LENGTH: 22
<212> TYPE: DNA
<213> ORGANISM: Homo sapiens

<400> SEQUENCE: 19
```

```
gcccagcgag gatatctgga ag                                          22
```

<210> SEQ ID NO 20
<211> LENGTH: 22
<212> TYPE: DNA
<213> ORGANISM: Homo sapiens

<400> SEQUENCE: 20

```
agcgcctccc tccactcgga ag                                          22
```

<210> SEQ ID NO 21
<211> LENGTH: 22
<212> TYPE: DNA
<213> ORGANISM: Homo sapiens

<400> SEQUENCE: 21

```
cgaacacaca acgtcttgga gc                                          22
```

<210> SEQ ID NO 22
<211> LENGTH: 22
<212> TYPE: DNA
<213> ORGANISM: Homo sapiens

<400> SEQUENCE: 22

```
gaccagatcc cggagttgga aa                                          22
```

<210> SEQ ID NO 23
<211> LENGTH: 19
<212> TYPE: DNA
<213> ORGANISM: Homo sapiens

<400> SEQUENCE: 23

```
cccaagtcct gcgcctcgc                                              19
```

<210> SEQ ID NO 24
<211> LENGTH: 19
<212> TYPE: DNA
<213> ORGANISM: Homo sapiens

<400> SEQUENCE: 24

```
gccttctctc cgtcctcgg                                              19
```

<210> SEQ ID NO 25
<211> LENGTH: 19
<212> TYPE: DNA
<213> ORGANISM: Homo sapiens

<400> SEQUENCE: 25

```
tctcctcgac ggagtcctc                                              19
```

<210> SEQ ID NO 26
<211> LENGTH: 19
<212> TYPE: DNA
<213> ORGANISM: Homo sapiens

<400> SEQUENCE: 26

```
cacagcccac tggtcctca                                              19
```

<210> SEQ ID NO 27
<211> LENGTH: 19
<212> TYPE: DNA
<213> ORGANISM: Homo sapiens

<400> SEQUENCE: 27
accagcccca ggtcctcgg                                                    19

<210> SEQ ID NO 28
<211> LENGTH: 22
<212> TYPE: DNA
<213> ORGANISM: Homo sapiens

<400> SEQUENCE: 28
gaagtctgag ggaaaccaga gt                                                22

<210> SEQ ID NO 29
<211> LENGTH: 22
<212> TYPE: DNA
<213> ORGANISM: Homo sapiens

<400> SEQUENCE: 29
tgggagattc ggagcgcagg ga                                                22

<210> SEQ ID NO 30
<211> LENGTH: 22
<212> TYPE: DNA
<213> ORGANISM: Homo sapiens

<400> SEQUENCE: 30
actatttgca taagaatagg ga                                                22

<210> SEQ ID NO 31
<211> LENGTH: 22
<212> TYPE: DNA
<213> ORGANISM: Homo sapiens

<400> SEQUENCE: 31
gctacaggga gagaaacaga gg                                                22

<210> SEQ ID NO 32
<211> LENGTH: 22
<212> TYPE: DNA
<213> ORGANISM: Homo sapiens

<400> SEQUENCE: 32
gagccccagg acgaaccaga gc                                                22

<210> SEQ ID NO 33
<211> LENGTH: 22
<212> TYPE: DNA
<213> ORGANISM: Homo sapiens

<400> SEQUENCE: 33
cgcagacagc cagacccagg gc                                                22

<210> SEQ ID NO 34
<211> LENGTH: 22
<212> TYPE: DNA
<213> ORGANISM: Homo sapiens

<400> SEQUENCE: 34
gtgagcaact tggagccaga ga                                                22

<210> SEQ ID NO 35
<211> LENGTH: 22
<212> TYPE: DNA
<213> ORGANISM: Homo sapiens

<400> SEQUENCE: 35
ccaagaactg cgtccacaga ga                                              22

<210> SEQ ID NO 36
<211> LENGTH: 22
<212> TYPE: DNA
<213> ORGANISM: Homo sapiens

<400> SEQUENCE: 36
tgagccaggg ttccccagg ga                                               22

<210> SEQ ID NO 37
<211> LENGTH: 94
<212> TYPE: DNA
<213> ORGANISM: Homo sapiens

<400> SEQUENCE: 37
gggcagagcg ctgcctctct gcaggccgtg tgctttgctc ggttgatctt gcagagccta     60
agacacaggc ccagagaggc agtgatcgcc aaag                                 94

<210> SEQ ID NO 38
<211> LENGTH: 94
<212> TYPE: DNA
<213> ORGANISM: Macaca mulatta

<400> SEQUENCE: 38
gggcagagcg ctgcctctct gcaggccgtg tgctttgctc ggttgatctt gcagagccta     60
agacacaggc ccagagaggc agtgatcgcc aaag                                 94

<210> SEQ ID NO 39
<211> LENGTH: 94
<212> TYPE: DNA
<213> ORGANISM: Mus sp.

<400> SEQUENCE: 39
gagcagagcg ctacctctct gcaggccctg tgctttgctc gttggatctt gaagagccta     60
agacacaggc ccagagaggc agagatcgcc aaag                                 94

<210> SEQ ID NO 40
<211> LENGTH: 94
<212> TYPE: DNA
<213> ORGANISM: Canis familiaris

<400> SEQUENCE: 40
gagcggagcg ctgcctctct gcaggccgtg tgctttgctc ggttgatctt gcagagccta     60
agacacaggc ccagagaggc agtgatcgcc aaag                                 94

<210> SEQ ID NO 41
<211> LENGTH: 24
<212> TYPE: DNA
<213> ORGANISM: Homo sapiens

<400> SEQUENCE: 41
ggaggagaca tggtgaacca gagt                                            24

<210> SEQ ID NO 42
<211> LENGTH: 24
<212> TYPE: DNA
<213> ORGANISM: Homo sapiens

```
<400> SEQUENCE: 42
ggaggagaca tggtgaaccc ccgt                                            24

<210> SEQ ID NO 43
<211> LENGTH: 109
<212> TYPE: DNA
<213> ORGANISM: Homo sapiens

<400> SEQUENCE: 43
ccgaccagct ggagatggtg accgagctgc tgggaggaga catggtgaac cagagtttca     60
tctgcgaccc ggacgacgag accttcatca aaaacatcat catccagga               109

<210> SEQ ID NO 44
<211> LENGTH: 550
<212> TYPE: RNA
<213> ORGANISM: Mus sp.

<400> SEQUENCE: 44
agacgaugac ggcggcggug gcaacuucuc caccgccgau cagcuggaga ugaugaccga     60
guuacuugga ggagacaugg ugaaccagag cuucaucugc gauccugacg acgagaccuu    120
caucaagaac aucaucaucc aggacuguau guggagcggu uucucagccg cugccaagcu    180
ggucucggag aagcuggccu ccuaccaggc ugcgcgcaaa gacagcacca gccugagccc    240
cgcccgcggg cacagcgucu gcuccaccuc cagccuguac cugcaggacc ucaccgccgc    300
cgcguccgag ugcauugacc ccucaguggu cuuucccuac ccgcucaacg acagcagcuc    360
gcccaaaucc uguaccucgu ccgauuccac ggccuucucu ccuuccucgg acucgcugcu    420
guccuccgag uccuccccac gggccagccc ugagccccua gugcugcaug aggagacacc    480
gcccaccacc agcagcgacu cugaagaaga gcaagaagau gaggaagaaa uugauguggu    540
gucuguggag                                                          550
```